(12) United States Patent
Gustafsson et al.

(10) Patent No.: US 7,873,477 B1
(45) Date of Patent: Jan. 18, 2011

(54) METHOD AND SYSTEM USING SYSTEMATICALLY VARIED DATA LIBRARIES

(75) Inventors: Claes Gustafsson, Belmont, CA (US); Sridhar Govindarajan, Redwood City, CA (US); Jeremy S. Minshull, Los Altos, CA (US); Jon E. Ness, Redwood City, CA (US); Robin A. Emig, Oakland, CA (US)

(73) Assignee: Codexis Mayflower Holdings, LLC, Redwood City, CA (US)

( * ) Notice: Subject to any disclaimer, the term of this patent is extended or adjusted under 35 U.S.C. 154(b) by 370 days.

(21) Appl. No.: 10/225,564

(22) Filed: Aug. 20, 2002

Related U.S. Application Data

(60) Provisional application No. 60/314,131, filed on Aug. 21, 2001, provisional application No. 60/316,812, filed on Aug. 31, 2001, provisional application No. 60/339,886, filed on Nov. 1, 2001, provisional application No. 60/392,511, filed on Jun. 27, 2002.

(51) Int. Cl.
*G06F 19/00* (2006.01)
*C40B 50/00* (2006.01)
*C40B 50/02* (2006.01)

(52) U.S. Cl. .............................. 702/19; 506/23; 506/24

(58) Field of Classification Search ...................... None
See application file for complete search history.

(56) References Cited

U.S. PATENT DOCUMENTS

| | | | |
|---|---|---|---|
| 4,959,312 A | 9/1990 | Sirotkin | |
| 5,043,272 A | 8/1991 | Hartly et al. | |
| 5,066,584 A | 11/1991 | Gyllenstein et al. | |
| 5,264,563 A | 11/1993 | Huse | |
| 5,506,793 A | 4/1996 | Straayer | |
| 5,521,077 A | 5/1996 | Kholsa | |
| 5,789,577 A | 8/1998 | Geysen | |
| 5,811,238 A * | 9/1998 | Stemmer et al. ................ 506/1 |
| 5,824,469 A | 10/1998 | Horowitz | |
| 5,825,978 A | 10/1998 | Digalakis et al. | |
| 5,864,810 A | 1/1999 | Digalakis et al. | |
| 5,866,363 A | 2/1999 | Pieczenik | |
| 5,869,644 A | 2/1999 | Shortle et al. | |
| 6,001,574 A | 12/1999 | Short et al. | |
| 6,030,779 A | 2/2000 | Short | |
| 6,054,267 A | 4/2000 | Short | |
| 6,055,498 A | 4/2000 | Neumeyer et al. | |
| 6,096,548 A | 8/2000 | Stemmer | |
| 6,117,679 A | 9/2000 | Stemmer | |
| 6,132,970 A | 10/2000 | Stemmer | |
| 6,153,410 A | 11/2000 | Arnold | |
| 6,159,690 A | 12/2000 | Borrebaeck et al. | |
| 6,188,965 B1 | 2/2001 | Mayo et al. | |
| 6,226,611 B1 | 5/2001 | Neumeyer et al. | |
| 6,256,607 B1 | 7/2001 | Digalakis et al. | |
| 6,269,312 B1 | 7/2001 | Mayo et al. | |
| 6,615,253 B1 | 9/2003 | Bowman-Amuah | |
| 7,165,041 B1 * | 1/2007 | Guheen et al. ................. 705/26 |
| 2007/0037214 A1 | 2/2007 | Luo et al. | |
| 2007/0178474 A1 * | 8/2007 | Cracauer et al. ............... 435/6 |

FOREIGN PATENT DOCUMENTS

| | | |
|---|---|---|
| WO | WO 90/00626 A1 | 1/1990 |
| WO | WO 92/06176 A1 | 4/1992 |
| WO | WO 00/00632 A1 | 1/2000 |
| WO | WO 00/23564 A2 | 4/2000 |
| WO | WO 00/42560 | 7/2000 |
| WO | WO 00/47612 A2 | 8/2000 |

OTHER PUBLICATIONS

Sheridan et al (Journal of Molecular Graphics (2000) vol. 18, pp. 320-334).*

Allawi et al. (1997) "Thermodynamics and NMR of internal G.T mismatches in DNA." Biochemistry, 36 10581-10594.

Arkin (1992) "An algorithm for protein engineering: Simulations of recursive ensemble mutagenesis." Proc Natl Acad Sci Aug. 15;89(16):7811-5.

Kayushin et al. (1996) "A convenient approach to the synthesis of trinucleotide phosphoroamidites-synthons for the generation of oligonucleotide/peptide libraries." Nucleic Acids Res. 24:3748-3755.

Moore et al. (2001) "Predicting crossover generation in DNA shuffling", PNAS, vol. 98, No. 6, pp. 3226-3231 (available at http://www.pnas.org/cgi/reprint/98/6/3226.pdf).

Santalucia (1998) "A unified view of polymer, dumbbell, and oligonucleotide DNA nearest-neighbor thermodynamics." PNAS, 95, 1460-1465.

Shao et al. (1998) "Random-priming in vitro recombination: an effective tool for directed evolution." Nucleic Acids Research 26(2):681-683.

U.S. Appl. No. 09/618,579, filed Jul. 18, 2000 "Methods for Making Character Strings, Polynucleotides and Polypeptides Having Desired Characteristics" Inventors: Selifonov et al.

(Continued)

*Primary Examiner*—Lori A Clow
(74) *Attorney, Agent, or Firm*—Weaver Austin Villeneuve & Sampson LLP

(57) ABSTRACT

Methods and systems for providing biological results in the form of systematically varied libraries of sequences or as data representing sequences or physical preparations of systematically varied libraries and/or selections from systematically varied libraries.

20 Claims, 16 Drawing Sheets

OTHER PUBLICATIONS

U.S. Appl. No. 10/232,770, filed Aug. 30, 2002 "Method and/or Apparatus for Determining Codons" Inventors: Robin A. Emig, et al.

U.S. Appl. No. 10/279,762, filed Oct. 23, 2002 "Method and Apparatus for Recombination Calculators" Inventors: Emily C. Mundorff, et al.

U.S. Appl. No. 10/607,817, filed Jun. 26, 2003 "Method and Apparatus for Sequence Backtranslating Using a Computer System" Inventors: Robin A. Emig, et al.

U.S. Appl. No. 60/284,407, filed Apr. 17, 2001 "Structure-Based Construction of Human Antibody Library" Inventor: Peizhi Luo.

U.S. Appl. No. 12/558,039, filed Sep. 11, 2009 "Method and System Using Systematically Varied Data Libraries" Inventors: Gustafsson et al.

Allawi et al. (1998) "Thermodynamics of internal C-T mismatches in DNA", *Nucleic Acids Research*, 26 2694-2701.

Minshull et al.(1999) *Current Opinion in Chemical Biology* 3(3):284-290.

Moreira (2002) "Genetic Algorithms for the Imitation of Genomic Styles in Protein Backtranslation", *Theoretical Computer Science* 322:297-312.

U.S. Office Action dated Apr. 25, 2005 issued in U.S. Appl. No. 10/232,770.

U.S. Office Action dated Nov. 29, 2005 issued in U.S. Appl. No. 10/232,770.

U.S. Office Action (Notice of Non-Compliant Amendment) dated Apr. 12, 2006 issued in U.S. Appl. No. 10/232,770.

U.S. Office Action Final dated Aug. 11, 2006 issued in U.S. Appl. No. 10/232,770.

US Office Action (Advisory Action) dated Oct. 30, 2006 issued in U.S. Appl. No. 10/232,770.

U.S. Office Action dated Jan. 4, 2007 issued in U.S. Appl. No. 10/232,770.

U.S. Office Action (Interview Summary) dated Feb. 15, 2007 issued in U.S. Appl. No. 10/232,770.

U.S. Office Action (Notice of Non-Compliant Amendment) dated Jun. 12, 2007 issued in U.S. Appl. No. 10/232,770.

U.S. Office Action Final dated Sep. 25, 2007 issued in U.S. Appl. No. 10/232,770.

U.S. Office Action dated Mar. 6, 2008 issued in U.S. Appl. No. 10/232,770.

U.S. Office Action dated Dec. 5, 2008 issued in U.S. Appl. No. 10/232,770.

U.S. Office Action Final dated Oct. 7, 2009 issued in U.S. Appl. No. 10/232,770.

U.S. Office Action (Interview Summary) dated Nov. 19, 2009 issued in U.S. Appl. No. 10/232,770.

U.S. Notice of Allowance dated Nov. 25, 2009 issued in U.S. Appl. No. 10/232,770.

\* cited by examiner

```
              Example MSF Aligned Amino Acid Sequence File Listing
MSF: 141    Type:  P    Check: 4981    ..
Name: ALK1_HUMAN          Len: 141      Check: 4590       Weight: 0
Name: BLE1_BACSP          Len: 141      Check: 2662       Weight: 0
//
             1                                                    50
ALK1_HUMAN   .MKSSGLFPF LVLLALGTLA PWAVEGSGKS FKAGVCPPKK SAQCLRYKKP
BLE1_BACSP   MLQSIPALP. .VGDIKKSIG FYCDKLGFTL VHHEDGFAVL MCNEVRIHLW
             51                                                  100
ALK1_HUMAN   ECQSDWQCPG KKRCCPDTCG IKCLDPVDTP NPTRRKPGKC PVTYGQCLML
BLE1_BACSP   EASDEGWR.S RSNDSPVCTG AESFIAGTAS CRIEVEGIDE LYQHIKPLGI
             101                                                 141
ALK1_HUMAN   NPPNFCEMDG QCKRDLKCCM GMCGKSCVSP VKA....... .
BLE1_BACSP   LHPNTSLKDQ WWDERDFAVI DPDNNLISFF QQIKS..... .
```

*FIG. 1*

```
                         Example PDB Input Data
HEADER     OXYGEN TRANSPORT                                      ODCH         ODCH   3
COMPND     HEMOGLOBIN (COBALT,DEOXY)                                          ODCH   4
SOURCE     HUMAN (HOMO SAPIENS)                                               ODCH   5
REMARK   1 REFERENCE 1                                                        ODCH   7
REMARK   1 TITL     STRUCTURE OF HUMAN DEOXY COBALT HAEMOGLOBIN               ODCH   9
REMARK   2 RESOLUTION. 2.50 ANGSTROMS.                                        ODCH  13
SEQRES   1 A  141   VAL LEU SER PRO ALA ASP LYS THR ASN VAL LYS ALA ALA       ODCH  18
SEQRES   2 A  141   TRP GLY LYS VAL GLY ALA HIS ALA GLY GLU TYR GLY ALA       ODCH  19
...
SEQRES   8 A  141   ARG VAL ASP PRO VAL ASN PHE LYS LEU LEU SER HIS CYS       ODCH  25
SEQRES   9 A  141   LEU LEU VAL THR LEU ALA ALA HIS LEU PRO ALA GLU PHE       ODCH  26
SEQRES  10 A  141   THR PRO ALA VAL HIS ALA SER LEU ASP LYS PHE LEU ALA       ODCH  27
SEQRES  11 A  141   SER VAL SER THR VAL LEU THR SER LYS TYR ARG               ODCH  28
SEQRES   1 B  146   VAL HIS LEU THR PRO GLU GLU LYS SER ALA VAL THR ALA       ODCH  29
SEQRES   2 B  146   LEU TRP GLY LYS VAL ASN VAL ASP GLU VAL GLY GLY GLU       ODCH  30
...
SEQRES  10 B  146   PHE GLY LYS GLU PHE THR PRO PRO VAL GLN ALA ALA TYR       ODCH  38
SEQRES  11 B  146   GLN LYS VAL VAL ALA GLY VAL ALA ASN ALA LEU ALA HIS       ODCH  39
SEQRES  12 B  146   LYS TYR HIS                                               ODCH  40
CRYST1    63.200   83.100   53.800  90.00  99.10  90.00 P 21         4        ODCH  41
ORIGX1      1.000000  0.000000  0.000000        0.00000                       ODCH  42
ORIGX2      0.000000  1.000000  0.000000        0.00000                       ODCH  43
ORIGX3      0.000000  0.000000  1.000000        0.00000                       ODCH  44
SCALE1      1.000000  0.000000  0.000000        0.00000                       ODCH  45
SCALE2      0.000000  1.000000  0.000000        0.00000                       ODCH  46
SCALE3      0.000000  0.000000  1.000000        0.00000                       ODCH  47
MASTER         12    0    0    0    0    0    0    6    0    0   23           ODCH  48
END                                                                           ODCH  49
```

*FIG. 2*

| Example SMILE Input(s) |
|---|
| CCCC(C(=O)O)CCC |
| NC(=N)c1ccccc1 |

*FIG. 3*

| Example Oligonucleotides Output File |
|---|
| Oligo-1-1-10    GTCGTC |
| Oligo-2-1-10    GTCGTC |
| Oligo-3-1-20    CTGCTGTTTCTGTTCAGCTCTGCTTATTCCCGTGGT |
| Oligo-4-1-20    CTGCTGTTTCTGTTCAGCTCTGCTTATTCCCGTGGT |
| Oligo-5-11-30   GAGTGAGAACACACATAGTGCTGCTTTGTGTGGTGCCCTTATTCGTCTCGACTTGTCTTT |
| Oligo-6-21-40   GTGTTTCGTCGTGATACACACAAGAGTGAGGTTGCTCATCGTTTTAAAGATTTGGGCGAA |
| Oligo-7-31-50   CCGTTGGTCATGGTCCGGAAATTTTACAAGAAGCGGGTTTAGAAATTTTGCTACTCGTTG |
| Oligo-8-41-60   GAACATTTTAAAGGCCTGGTACTGGTTGCCTTTTCTCAGTATCTGCAGCAGTGTCCATTT |
| Oligo-9-51-70   ATGAAGCAAGTGATTAAAATGTACGAGAAGTTTACCTGTGACGACGTCTATGACTCTTTT |
| ... |
| Oligo-52-481-500 CTGAACCGTTTGTGCGTGCTGCATGAGAAAACACCGGTTTCAGAAAAAGTCACGAAATGC |
| Oligo-53-491-510 TCCTGCTGCCAACTGGTCGCTAAGGCACGTCGTAAAGCACTGAAAAAGACTTTGGCCACA |
| Oligo-54-501-520 TGCACGGAATCGCTGGTCAACCGTCGTCCTTGCTTTTCTGCGTTAGAACTGGATGAAGCT |

*FIG. 4*

| Example Shuffling Parameters Output File |
|---|
| Apparatus. Stratagen Robocycler |
| Tubes   Cat # 7756-4674 |
| Autoclaved ultra-filtered water (pH 7.0).   20.7μl |
| 10x Assembly Buffer, lot# 37              2.5μl |
| dNTP mix, 25 mM, lot #62.                  0.2μl |
| Herculase Polymerase 5u/μl Cat #45-1388  0.2μl |
| Oligonucleotide mix:                       1.0μl |
| Temperature 1    94°C    15sec |
| Temperature 2    48°C    45sec |
| Temperature 3    68°C    45sec |
|         Repeat temperatures 1 through 3 25 times |
| Temperature 4    68°C    240sec |

*FIG. 5*

| Example Machine Instruction Code Output File |
|---|

Air Volume (µl);0;0;SYR.Max Volume
Filling Speed (µl/s);7.5;Syr.Min Speed;Syr.Max Speed
Filling Strokes ();3;0;99
Injection Speed (µl/s),5,SYR Min Speed;SYR Max Speed
Post Inject Delay (ms),500,0,99000
Post Clean with Solvent 1 (),3,0,99
WAIT_SYNC_SIG(Start,)
SWITCH_EVENT(SW-Out2,On,500,)
WAIT_SYNC_SIG(Start,)
SWITCH_EVENT(SW-Out1,On,500,)
WAIT(12,)
REPEAT(48,)
GET_SAMPLE(HudsonMT,SL.index,SL.volume,Air Volume,,,Filling Speed,,,Filling Strokes,Off,,,)
INC_INDEX()
INC_INDEX()
INJ_SAMPLE(LC Vlv1,Inject,Injectd2,,,,Injection Speed,Post Inject Delay,,)
SWITCH_EVENT(SW-Out1,On,500,)
CLEAN_SYR(Wash1,Post Clean with Solvent 1,,,,,,)
ASPIRATE_SYR(SYR Max Volume,,Filling Speed,,)
SWITCH_INJ(LC Vlv1,Active,,)
WAIT_SYNC_SIG(Start2,)
SWITCH_INJ(LC Vlv1,Standby,,)
WAIT(4,)
MOVETO_OBJECT(LC Vlv1,,,)
DISPENSE_SYR(SYR Max Volume,Injection Speed,)
END()
CLEANUP(Wash1,Off,Off,On,Off,Off,Off,On,)

*FIG. 6*

| Example Structure Coordinates Output File |||||||||||
|---|---|---|---|---|---|---|---|---|---|---|
| ATOM | 4 | N | MET | A | 1 | 44.059 | -5.585 | -29.335 | 1.00 34.35 | N |
| ATOM | 5 | CA | MET | A | 1 | 45.028 | -4.884 | -28.500 | 1.00 34.60 | C |
| ATOM | 6 | C | MET | A | 1 | 44.436 | -4.641 | -27.114 | 1.00 36.05 | C |
| ATOM | 7 | O | MET | A | 1 | 43.291 | -4.183 | -26.978 | 1.00 36.59 | O |
| ATOM | 8 | CB | MET | A | 1 | 45.419 | -3.545 | -29.137 | 1.00 33.15 | C |
| ATOM | 9 | CG | MET | A | 1 | 45.989 | -3.666 | -30.546 | 1.00 31.11 | C |
| ATOM | 10 | SD | MET | A | 1 | 47.242 | -4.951 | -30.682 | 1.00 26.24 | S |
| ATOM | 11 | CE | MET | A | 1 | 48.619 | -4.208 | -29.821 | 1.00 29.86 | C |
| ATOM | 12 | N | | A | 2 | 45.222 | -4.960 | -26.089 | 1.00 36.41 | N |
| ATOM | 13 | CA | | A | 2 | 44.791 | -4.800 | -24.707 | 1.00 36.70 | C |
| ATOM | 14 | C | | A | 2 | 44.702 | -3.329 | -24.341 | 1.00 38.12 | C |
| ATOM | 15 | O | | A | 2 | 43.923 | -2.929 | -23.472 | 1.00 37.57 | O |
| ATOM | 20 | N | | A | 3 | 45.521 | -2.524 | -25.006 | 1.00 39.14 | N |
| ATOM | 21 | CA | | A | 3 | 45.510 | -1.107 | -24.732 | 1.00 39.62 | C |
| ATOM | 22 | C | | A | 3 | 44.901 | -0.360 | -25.893 | 1.00 39.46 | C |
| ATOM | 23 | O | | A | 3 | 44.194 | -0.927 | -26.728 | 1.00 39.09 | O |
| ATOM | 24 | N | | A | 4 | 45.185 | 0.930 | -25.939 | 1.00 39.09 | N |
| ATOM | 25 | CA | | A | 4 | 44.689 | 1.778 | -26.994 | 1.00 38.12 | C |
| ATOM | 26 | C | | A | 4 | 45.750 | 2.833 | -27.190 | 1.00 38.23 | C |
| ATOM | 27 | O | | A | 4 | 45.740 | 3.853 | -26.511 | 1.00 38.98 | O |
| ATOM | 31 | N | | A | 5 | 46.679 | 2.573 | -28.103 | 1.00 38.15 | N |
| ATOM | 32 | CA | | A | 5 | 47.763 | 3.509 | -28.351 | 1.00 38.45 | C |
| ATOM | 33 | C | | A | 5 | 47.350 | 4.686 | -29.211 | 1.00 39.11 | C |
| ATOM | 34 | O | | A | 5 | 46.765 | 4.523 | -30.278 | 1.00 40.56 | O |
| ATOM | 40 | N | | A | 6 | 47.660 | 5.879 | -28.726 | 1.00 39.25 | N |
| ATOM | 41 | CA | | A | 6 | 47.365 | 7.087 | -29.463 | 1.00 37.58 | C |
| ATOM | 42 | C | | A | 6 | 48.714 | 7.550 | -29.962 | 1.00 37.89 | C |
| ATOM | 43 | O | | A | 6 | 49.746 | 6.945 | -29.649 | 1.00 38.51 | O |
| ATOM | 44 | N | | A | 7 | 48.755 | 8.623 | -30.744 | 1.00 38.05 | N |
| ATOM | 45 | CA | | A | 7 | 50.054 | 9.087 | -31.240 | 1.00 38.55 | C |
| ATOM | 46 | C | | A | 7 | 50.604 | 10.019 | -30.188 | 1.00 38.36 | C |
| ATOM | 47 | O | | A | 7 | 51.609 | 10.702 | -30.390 | 1.00 38.71 | O |

*FIG. 7*

| 101a | Name and/or Description of Operation 1<br>(e.g., Calculate Shufflability of Parents)<br>Identifying Relevant Diversity<br>*(click here to select)* |
|---|---|
| 101b | Name and/or Description of Operation 2<br>(e.g., Determine Degenerate Oligonucleotides)<br>*(click here to select)* |
| 101c | Name and/or Description of Operation 3<br>(e.g., Identifying Crossover Points)<br>*(click here to select)* |
| 101d | Name and/or Description of Operation N<br>(e.g., Identify Relevant Diversity)<br>*(click here to select)* |
| 102 | License and Intellectual Property Rights<br>Statement Summary<br>(click here to view full statement) |
| 103 | Login Name: \|_____\|<br>Password: \|_____\| |

*FIG. 10A*

| 105 | The operation you requested requires an input file in one or more of the following formats: (MSF, PDB, etc.) *(click here to attach input file)* |

*FIG. 10B*

| 110 | One or more operations you have selected may be enhanced by using intermediate sequence data and/or proprietary analysis methods. As explained in the License Agreement, performance of this operation does not give you any rights in this intermediate data or proprietary analysis methods. |

| 112 | *(Click here if you understand and agree to the conditions regarding Intermediate Data and Proprietary Routines in the Licensee Agreement.)* |

| 114 | *(Click here if you do not agree to the conditions regarding Intermediate Data in the Licensee Agreement. If possible, your requested analysis will be performed without Intermediate Data; otherwise, your request for this analysis will be cancelled.)* |

*FIG. 10C*

| 120 | Your request has been accepted and is being processed |
| --- | --- |
| 122 | Your results will be ready in approximately ___ minutes. |
| 124 | This operation will be charged to account: AccountId *(click here to change account information)* |
| 126 | The expected charge for this operation is ___. |
| 128 | Results from this operation will be delivered to _____ *(click here to change results destination)* |

METHOD AND SYSTEM USING SYSTEMATICALLY VARIED DATA LIBRARIES

CROSS REFERENCE TO RELATED APPLICATIONS

This application claims priority from provisional patent application U.S. Ser. No. 60/314,131, filed 21 Aug. 2001 and is incorporated herein by reference for all purposes.

This application claims priority from provisional patent application U.S. Ser. No. 60/316,812, filed 31 Aug. 2001 and is incorporated herein by reference for all purposes.

This application claims priority from provisional patent application U.S. Ser. No. 60/339,886, filed 1 Nov. 2001 and is incorporated herein by reference for all purposes.

This application claims priority from provisional patent application U.S. Ser. No. 60/392,511, filed 27 Jun. 2002, and is incorporated herein by reference for all purposes.

COPYRIGHT NOTICE

Pursuant to 37 C.F.R. 1.71(e), Applicants note that a portion of this disclosure contains material that is subject to copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to methods and/or systems for providing systematically varied libraries of biologic sequences and/or or biological polymers (e.g., RNA, DNA, proteins, polypeptides, oligonucleotides, etc., corresponding to those sequences) or data representing or enabling systematically varied libraries. In specific embodiments, the invention involves a method and/or system for providing or enabling ordering of such libraries over a communication network, such as the world-wide Internet. In other embodiments, the invention involves a method and/or system enabling ordering of a newly determined biologic sequence or polymer over a communication network, such as the Internet. In other specific embodiments, the invention involves a method and/or system for providing systematically varied libraries of biologic sequences as one or more mixtures or an arrangement of physical preparations of biologic polymers. In further embodiments, the invention includes methods and/or systems for providing associated services, such as billing, reporting, managing licensing agreements, etc.

BACKGROUND OF THE INVENTION

Companies and institutions performing biologic and/or chemical research or development activities generally employ outside providers of materials and/or analysis. These providers supply such things as specialized analysis, particular reagents or enzymes, cell lines or living research organisms with particular characteristics, specific compounds or molecules, or cassettes containing a variety of compounds (i.e. pharmaceutical or enzymatic agents) to aid in assaying a group of compounds against a particular target. Other providers perform synthesis of particular molecules, such as oligonucleotides or polypeptides by specifying their sequences using a communication channel.

However, there are a number of limitations to most such services. In particular, such services generally provide either preexisting compounds or compounds that are sequence-specified by the user. Customers therefore cannot use such services to create entirely new compounds. Using outside services to assist in creating entirely new compounds is generally an expensive and highly customized process of collaborative research. The end product of such research collaborations is generally a single molecule or limited set of screened molecules that are thought to be of interest.

Another limitation to using outside services, including collaborative research arrangements, is that institutions performing biologic and/or chemical research or development activities are at times often highly protective of their activities. A company that wishes to target a particular human enzyme or gene with a particular type of compound, for example, may not wish to reveal both the target and the characteristics of the candidate compound. However, in most molecular development projects, a target is provided to the service provider for screening purposes. Thus, there remains a continuing need for novel methods and/or systems for supplying chemical and/or biologic services.

Communication Using Networked Information Appliances

The Internet comprises computers, information appliances, and computer networks that are interconnected through communication links. The interconnected computers exchange information using various services, such as electronic mail, ftp, the World Wide Web ("WWW") and other services, including secure services. The WWW service can be understood as allowing a server computer system (e.g., a Web server or a Web site) to send web pages of information to a remote client information appliance or computer system. The remote client computer system can then display the web pages. Generally, each resource (e.g., computer or web page) of the WWW is uniquely identifiable by a Uniform Resource Locator ("URL"). To view or interact with a specific web page, a client computer system specifies a URL for that web page in a request. The request is forwarded to a server that supports that web page. When the server receives the request, it sends that web page to the client information system. When the client computer system receives that web page, it can display the web page using a browser or can interact with the web page or interface as otherwise provided. A browser is a logic module that effects the requesting of web pages and displaying or interacting with web pages.

Currently, displayable web pages are typically defined using a Hyper Text Markup Language ("HTML"). HTML provides a standard set of tags that define how a web page is to be displayed. An HTML document contains various tags that control the displaying of text, graphics, controls, and other features. The HTML document may contain URLs of other Web pages available on that server computer system or other server computer systems. URLs can also indicate other types of interfaces, including such things as CGI scripts or executable interfaces, that information appliances use to communicate with remote information appliances or servers without necessarily displaying information to a user.

The Internet is especially conducive to providing information services to one or more remote customers. Services can include items (e.g., music or stock quotes) that are delivered electronically to a purchaser over the Internet. Services can also include handling orders for items (e.g., groceries, books, or chemical or biologic compounds, etc.) that may be delivered through conventional distribution channels (e.g., a common carrier). Services may also include handling orders for items, such as airline or theater reservations, that a purchaser accesses at a later time. A server computer system may provide an electronic version of an interface that lists items or services that are available. A user or a potential purchaser may access the interface using a browser and select various items of interest. When the user has completed selecting the items desired, the server computer system may then prompt the user for information needed to complete the service. This transaction-specific order information may include the purchaser's name or other identification, an identification for payment (such as a corporate purchase order number or account number), or additional information needed to complete the service, such as flight information.

NCBI Databases and Software

Among services of particular interest that can be provided over the internet and over other networks are biological data and biological databases. Such services include a variety of services provided by the National Center for Biotechnology Information (NCBI) of the National Institutes of Health (NIH). NCBI is charged with creating automated systems for storing and analyzing knowledge about molecular biology, biochemistry, and genetics; facilitating the use of such databases and software by the research and medical community; coordinating efforts to gather biotechnology information both nationally and internationally; and performing research into advanced methods of computer-based information processing for analyzing the structure and function of biologically important molecules.

For example, NCBI holds responsibility for the GenBank DNA sequence database. The database has been constructed from sequences submitted by individual laboratories and by data exchange with the international nucleotide sequence databases, the European Molecular Biology Laboratory (EMBL) and the DNA Database of Japan (DDBJ), and includes patent sequence data submitted to the U.S. patent office. In addition to GenBank, NCBI supports and distributes a variety of databases for the medical and scientific communities. These include the Online Mendelian Inheritance in Man (OMIM), the Molecular Modeling Database (MMDB) of 3D protein structures, the Unique Human Gene Sequence Collection (UniGene), a Gene Map of the Human Genome, the Taxonomy Browser, and the Cancer Genome Anatomy Project (CGAP), in collaboration with the National Cancer Institute. Entrez is NCBI's search and retrieval system that provides users with integrated access to sequence, mapping, taxonomy, and structural data. Entrez also provides graphical views of sequences and chromosome maps. A feature of Entrez is the ability to retrieve related sequences, structures, and references. BLAST is a program for sequence similarity searching developed at NCBI for identifying genes and genetic features that can execute sequence searches against the entire DNA database. Additional software tools provided by NCBI include: Open Reading Frame Finder (ORF Finder), Electronic PCR, and the sequence submission tools, Sequin and BankIt. NCBI's various databases and software tools are available from the WWW or by FTP or by e-mail servers. Further information is available at www(.)ncbi(.)nlm(.)nih(.) gov.

CHIME

Some biologic data available over the internet is data that is generally viewed with a special browser "plug-in" or other executable code. One example of such a system is CHIME, a browser plug-in that allows an interactive virtual 3-dimensional display of molecular structures, including biological molecular structures. Further information regarding CHIME is available at www(.)mdlchime(.)com(/)chime/.

Online Oligos, Gene, or Protein Ordering

A variety of companies and institutions provide online systems for ordering biological compounds. Examples of such systems can be found at www(.)genosys(.)com(/)oligo_custinfo.cfm or www(.)genomictechnologies(.)com/Qbrowser2_FP(.)html. Typically, these systems accept some descriptor of a desired biological compound (such as an oligo, DNA strand, RNA strand, amino acid sequence, etc.) and then the requested compound is manufactured and is shipped to the customer in a liquid solution or other appropriate form.

SUMMARY

The present invention, in specific embodiments, involves methods and/or systems for providing systematically varied libraries of biologic sequence data and/or corresponding biological molecules and/or data enabling a client to generate systematically varied libraries. Thus, in specific embodiments, the present invention provides a method and/or system that allows a customer to request new biologic sequences or biologic sequences molecules from a service provider and to receive results that represent or enable or comprise a systematically varied library of biologic sequences. Generally, sequence library results will largely or entirely be made of sequences that did not previously exist and that were not specified by a user and therefore such libraries are referred to as "new" in this discussion. Requests for new sequences or data or instructions enabling the same and/or any necessary input data can be carried over a data communication network, such as the Internet. In alternative embodiments, such requests can be conveyed by other convenient means, e.g., an intranet, network, or via hand delivery.

In specific embodiments of the invention, a client system is provided with a set of interfaces from a server system that allows the client system to indicate desired operations related to diversity generation. A client system according to specific embodiments of the invention, presents information received from a server system that identifies analysis and/or operations available at the server system. In response to a user input, or automatically in some embodiments, a client system sends to a server system necessary initial information and a request to perform a diversity generation operation. Diversity generation operations can be deterministic operations, where a large group of systematically varying sequences are identified by a rule set or non-deterministic where a group of systematically varying sequences are generated through shuffling or other non-deterministic recombination methods. The server system then performs a requested operation and returns results to a destination indicated by a user. Results can include computer encoded data and/or compounds, molecules or mixtures, according to specific embodiments of the invention. For example, the results can include digital logic instructions able to instruct a sequence system to prepare a systematically varied library. For example, the digital logic instructions are instructions useable by an oligonucleotide synthesizer, a parallel gene synthesis device, a polypeptide synthesizer, an automated shuffling system (e.g., a shuffling machine) and/ or an automated PCR system.

In specific embodiments, the analysis or operation provided by the server system may be done entirely in a digital information processing system (e.g., one or more computers). Alternatively, portions of the analysis or operation may be done using physical diversity generation techniques, such as, for example, a "wet" shuffling reaction or parallel gene synthesis reaction. Alternative, a server system can use a combination of digital information processing and physical techniques to prepare the final result.

Results from a server system can be provided to a client as one or more data files. Such files may either directly represent a systematically varied library of biologic sequences, or may structurally describe one or more members of such a library, or may provide processing parameters enabling a client to generate such a systematically varied library using a synthesis system, or can contain machine instructions that can be directly used by an automated system for generating systematically varied libraries of sequence data. According to further embodiments, results can also be provided to a client as one or more chemical or biological preparations either containing a mixture of a library of systematically varied biologic sequences or containing separate preparations (generally carried in a compartmentalized container, such as an array or cassette or on a fixed media) of member sequences or groups of sequences in a systematically varied library of sequences. In a further embodiment, results can also comprise just one or a few new sequences selected at a server side from a systematically varied library of sequences.

A systematically varied library according to specific embodiments of the present invention will be understood from the teachings herein as comprising two or more different sequences (often 10's or 100's or 1000's) that are generated according to some diversity generation operation. For example, a digital or chemical shuffling reaction as described in references cited herein of parent oligonucleotides will produce shuffled products that are implicitly systematically varied. As is described in cited references, a shuffling reaction, through random recombination, will produce up to all possible combinations of the position variance in the parent sequences. In the art, a unique sequence in a systematically varied library of sequences is sometimes referred as a "clone."

Alternatively, a systematically varied library can be produced by a more explicit diversity generation operation. For example, from one or multiple parent sequences, a user can specify one or more sequence positions where diversity is desired and can optionally indicated the diversity desired and other characteristics such as tied positions. A diversity generation operation in this example will generally combinatorially produce sequences that contain all different combinations of the desired variations at those locations. Thus, a systematically varied library in this example can include a set of related systematically varied genes that are suitable to be created using parallel gene synthesis.

A systematically varied library according to specific embodiments of the present invention can further be screened or selected according to a variety of techniques to produce a systematically varied library that is a subset of the original systematically varied library. For example, two genes that have 29 positions of sequence diversity between them can generate up to 29! ($8.8 \times 10^{30}$) different clones in a un-screened systematically varied library. A variety of screening and/or pruning techniques can be used to reduce a systematically varied library of interest to perhaps a few dozen or a few thousand clones of interest, such as clones that are believed to produce proteins that will fold or proteins that have activity at a particular pH or oligonucleotides that do not include unwanted stop codons or other sequence characteristics. Screening and/or pruning techniques can be performed after the initial diversity generation operation is complete or as part of or intermediate to a diversity generation operation in order to reduce the amount of data handled or the amount of sequences synthesized.

The input to a system or method according to specific embodiments of the invention will typically be digital data, but in some embodiments may be a molecule or mixture of molecules of interest. Some initial input data or requests are generally provided by a client, but portions of the input can be derived from other sources such as publicly available biologic sequence data banks. Input data, in the case of digital data, can be obtained by a system or method according to specific embodiments of the present invention over a network, such as the Internet.

According to various specific embodiments, both the input and/or results can be in the form of functional data. Such data can indicate, as input, desired functional parameters of a resulting enzyme. Likewise, output data can be in the form of functional parameters that can be used to direct a diversity generating procedure. Specific examples are provided below.

In further embodiments, the present invention may be understood in the context of providing systematically varied biologic sequence libraries or information for generating such libraries over a communication media. An important application for the present invention, and an independent embodiment, is in the field of providing biologic data services over the Internet, optionally using Internet media protocols and formats, such as HTTP, RTTP, XML, HTML, dHTML, VRML, or image, audio, or video formats etc. However, using the teachings provided herein, it will be understood by those of skill in the art that the methods and apparatus of the present invention could be advantageously used in other related situations where users access content over a communication channel, such as modem access systems, institutional network systems, wireless systems, telephone systems, etc.

The present invention is involved with a number of unique methods and/or systems that can be used together or independently to provide systematically varied biologic sequences and/or data representing such sequences and/or data that can assist in synthesis of such sequences. In specific embodiments, the present invention can be understood as involving new business methods related to providing biologic sequences. Thus, the present invention, in specific embodiments involves one or more methods for conducting transactions related to systematically varied libraries of biological sequences. According to various embodiments of the present invention, a number of different customer input, delivered output, and processing options are possible. These methods generally have in common that the operations provided by the service provider involve some type of diversity generation and/or diversity analysis. These methods also generally have in common that the results provided to a client are directed to systematically libraries of new biologic sequences or to a new biologic sequence selected from a systematically varied library of sequences.

The invention and various specific aspects and embodiments will be better understood with reference to the following drawings and detailed descriptions. In different figures, similarly numbered items are intended to represent similar functions within the scope of the teachings provided herein. In some of the drawings and detailed descriptions below, the present invention is described in terms of the important independent embodiment of a system operating on a digital data network. This should not be taken to limit the invention, which, using the teachings provided herein, can be applied to other situations, such as cable television networks, wireless networks, telephone communications, etc. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification. The functional aspects of the invention that are implemented on a computer, as will be understood from the teachings herein, may be implemented or accomplished using any appropriate implementation environment or programming language, such as C, C++, Cobol, Pascal, Java, Java-script, HTML, XML, dHTML, assembly or machine code programming, etc. All references, publications, patents, and patent applications cited herein are hereby incorporated by reference in their entirety for all purposes.

Furthermore, in some aspects, the present invention is described in terms of client/server systems. A number of computing systems and computing architectures are described in the art as client/server art. For the purposes of this description, client/server should be understood to include any architecture or configuration wherein a program or device (e.g., a client) accesses another remote or separate program or device that is providing the desired service (e.g., a server).

BRIEF DESCRIPTION OF THE DRAWINGS

FIG. 1 illustrates an example of a partial input data file in MSF format that may be used according to specific embodiments of the invention.

FIG. 2 illustrates an example of a partial input data file in PDB format that may be used according to specific embodiments of the invention.

FIG. 3 illustrates an example of a partial input data in SMILES format that that may be used according to specific embodiments of the invention.

FIG. 4 illustrates an example of a partial output data file of oligonucleotides that may be provided according to specific embodiments of the invention.

FIG. 5 illustrates an example of a partial output data file of shuffling parameters that may be provided according to specific embodiments of the invention.

FIG. 6 illustrates an example of a partial output data file of machine instructions according to specific embodiments of the invention.

FIG. 7 illustrates an example of a partial output data file of structure coordinates that may be provided according to specific embodiments of the invention.

FIG. 10A-D are block diagrams illustrating example graphical interfaces according to specific embodiments of the present invention.

FIG. 11 is a flow diagram of a routine performed at a server system to generate interfaces that allow a customer to access recombination or analysis operations according to specific embodiments of the present invention.

DESCRIPTION OF SPECIFIC EMBODIMENTS

Figure 8A:
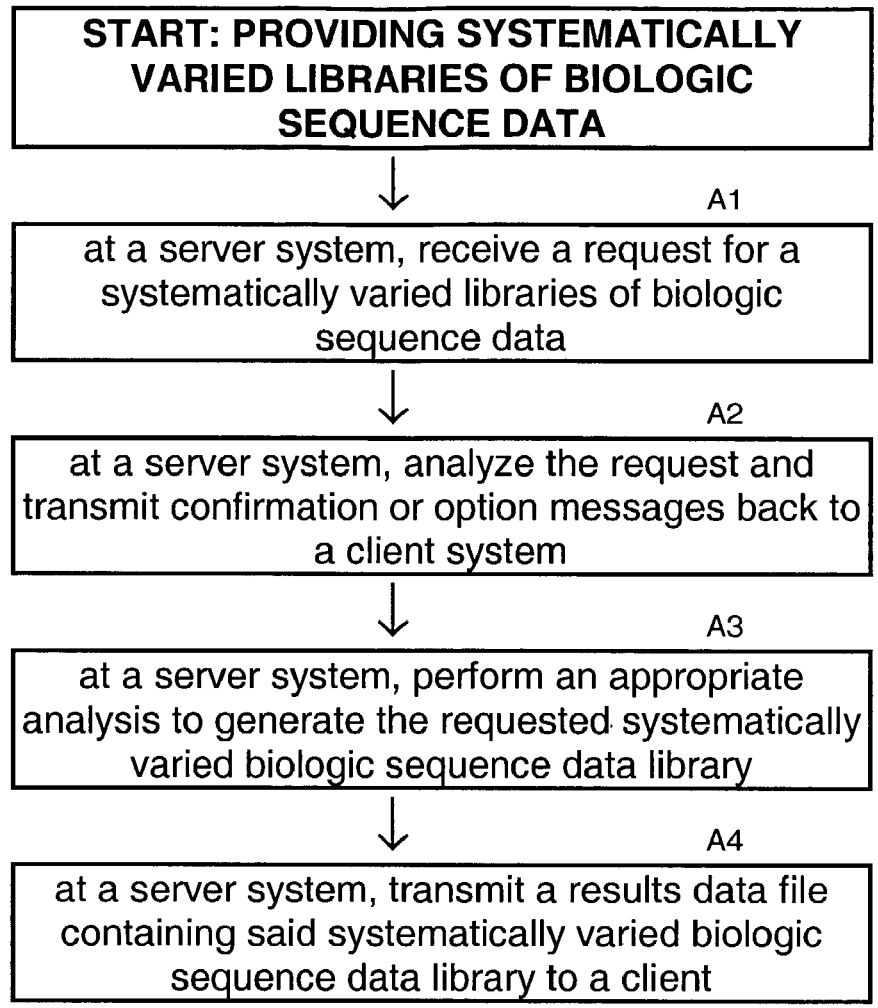
FIG. 8A-B are flow charts illustrating methods of providing systematically varied library results using a network according to specific embodiments of the invention.

The present invention, in various embodiments, involves providing or obtaining systematically varied libraries of biologic sequence, or data representing or facilitating creation of such sequences. In specific embodiments, provision of such systematically varied libraries can be facilitated using various information processing methods and systems as described herein, including communication over a network. In various specific embodiments, such systematically varied libraries can be generated using, either entirely or in part, data provided by a client. In various other specific embodiments, such systematically varied libraries can be generated using, either entirely or in part, initial sequence data available from various commercial or public biologic databases.

In further specific embodiments, the present invention can comprise a method and/or system for providing or obtaining systematically varied libraries of biologic sequences in a client/server information processing environment using a network. According to specific embodiments of the present invention, a system allows access by customers to sophisticated and/or proprietary biologic analysis or synthesis including recombination or shuffling routines over a network, while optionally allowing a service provider to keep those routines secret. According to further specific embodiments of the invention, the invention can also provide a user with recombination or analysis results wherein intermediate data is used to facilitate or create the results, while optionally keeping that intermediate data secret from the customer. Thus, the invention allows a server to reduce the amount of sensitive information that is exposed to a client system or a user/customer on a client system. According to further specific embodiments of the invention, the invention can also provide a user with recombination or analysis results from a user's initial data, while keeping that user's initial data secret. According to further specific embodiments of the invention, the invention can also provide a user with systematically varied library results, while allowing a user to keep the user's target functionality or screening methods secret.

Examples of methods for conducting such transactions, according to specific embodiments of the present invention, grouped according to the outputs provided, include: (1) A purchaser using an information appliance in communication with a service provider supplies or identifies one or more biologic sequence molecules of interest, e.g. polypeptides, DNA, RNA, oligonucleotides, biologic sequence families, etc. For a consideration, the service provider prepares a systematically varied library from the identified sequence(s) of interest. This library is supplied to the customer as a physical library of systematically varied compounds, either as one or more mixtures or separate preparations in a cassette or in a fixed media. For example, the data returned to the customer could be a set of data representing oligonucleotide sequences that can be input directly into a biologic molecule synthesizer. The resulting synthesized oligonucleotide sequences can be used in a shuffling or mutation reaction, or, e.g., in gene synthesizer for parallel gene synthesis. The customer can use any physical library which is produced to run further analysis, such as screening for a particular activity or characteristic.

As an alternative input, a customer may supply functional characteristics of, for example, a protein or polypeptide, either alone or with some sequence data. The service provider then analyzes the functional data (either alone or along with sequence data) and the service provider identifies publicly available or proprietary sequences to include in a diversity generation reaction and returns a systematically varied library to the purchaser. Similarly, a customer can provide a functional description of a desired end-product, such as a polypeptide, and the service provider can use that functional description to identify parents, perform a diversity generation operation, optionally perform some screening, and return systematically varied library results back to a user. Such systematically varied library can comprise a variety of different biologic molecules, such as genes, oligonucleotides, or polypeptides.

(2) A purchaser using an information appliance in communication with a service provider supplies or identifies one or more biologic sequence molecules of interest or other input as described herein. For a consideration, the service provider computes a systematically varied library from sequence(s) of interest and this library is supplied to the customer as digital data. This digital data may be encoded in a variety of formats, including formats that the customer can use directly in an automated synthesis device. For example, the data returned to the customer could be a set of data representing oligonucleotide sequences that can be input directly into a biologic molecule synthesizer and the resulting synthesized oligonucleotide sequences can be used in a shuffling reaction, or in a gene synthesizer for parallel gene synthesis.

(3) A purchaser, using an information appliance in communication with a service provider, can supply input in any of the forms described above. For a consideration, the service provider computes a number of operating parameters for enabling a reaction to produce a systematically varied library of interest. These parameters can include such things as annealing temperature, number of cycles, sequence extension times, etc. This digital data may be encoded in a variety of formats, including formats that the customer can use directly in an automated synthesis device for diversity generating reactions such as, but not limited to, directed evolution and/or parallel gene synthesis.

A further advantage that will be understood from the teachings herein is that in specific embodiments, the present invention can allow a biologic service provider to provide biologic analysis and/or libraries using data and/or methods that reside at a server side system but are never made known or accessible to a customer. For example, in some recombination methods, it is desirable to use either intermediate sequences, bridging sequences, or homologous sequences (either synthetic or from nature) during the recombination reaction. According to specific embodiments of the invention, the invention can provide a user a systematically varied library result of an input, optionally while using intermediate or bridging sequences that are never made available to the user.

Similarly, in specific embodiments, the present invention can allow a biologic service provider to provide biologic analysis and/or systematically varied libraries based on data received from a client, while preserving confidentiality of the data received from the client and of the results provided to the client. Thus, according to specific embodiments of the present invention, a biologic sequence library provider can provide libraries of never-before synthesized sequences while preserving the secrecy and confidentiality of both the clients input sequence data and any provided output sequence data.

Furthermore, according to specific embodiments of the present invention, a customer can utilize diversity generation services of a service provider without ever revealing to the service provider the desired uses for a particular compound or the methods of screening used by the customer to identify most desirable candidates. According to specific embodiments, a customer can therefore take advantage of the diversity generating abilities of a service provider, possibly over several iterations, without ever revealing what the customer wishes to keep as secret regarding targets characteristics of a final compound or screening techniques the customer may used in iteratively screening systematically varied library results and requesting new libraries.

Generating Libraries from Existing Databases

According to a further specific embodiments, the invention can allow a customer to order systematically varied libraries generated entirely or in part from existing biologic sequences, such as sequences selected or identified from external sources, for example publicly available databases. A method according to this embodiment involves: (1) Identifying a class or group of classes of genes, where class indicates a cluster of genes with some sequence homology (e.g., for example, >20%). Identification may be done through such methods as searching through sequences in available databases, such as patent databases; (2) For an identified class, using an aligned list of the homologs to identify relevant amino acid diversity (e.g., for example, using degenerate oligonucleotide design methods discussed in co-assigned patent applications.) According to specific embodiments of the present invention, this data itself can be sold/provided as an end product to a customer so that the customer can do further analysis to identify sequences of interest.

According to further embodiments of the present invention, services provided by the service provider can continue by: (3) using the aligned homologs and amino acid diversity data to generate a set of oligonucleotides that will combine to produce genes that will translate to all desired possible combinations of the initial sequences. This data or synthesized molecules could be provided as a product to a customer.

According to further embodiments of the present invention, services provided by the service provider can continue by: (4) creating systematically varied libraries from the oligonucleotides without having ever synthesized or directly used the original sequences (which may be patented or otherwise protected) and provide these libraries to clients. Again, this data or synthesized molecules could be provided as a product to a customer.

According to further embodiments of the present invention, services provided by the service provider can continue by: (5) screening and/or sorting libraries for folding (such as by FACS and/or GFP) or for other characteristics and these screened and/or sorted libraries can be provided or sold to clients.

(6) Likewise, according to further embodiments of the present invention, screened libraries can be assayed for a subset of simple related high throughput (HTP) functional surrogate assays. In this embodiment, a provider can provide a number of different services, such as: (a) provide functionally maximally distributed clones to be assayed for 'real' function by a customer, where the feedback from the customer would implicate the ideal functional clones in the library based on function-sequence mapping; (b) provide data for relationship sequence-function to extract hypothetical 'ideal' clone; (c) provide specific clones with postulated function in that library.

1. Examples of Inputs and Results According to Specific Embodiments of the Present Invention According to specific embodiments of the present invention, a request from a customer will typically be transmitted as a data file, usually using a computer understandable media, such as a network transmission, email transmission, or other data media, such as data storage media. For example, the data returned to the customer could be a set of data representing oligonucleotide sequences that can be input directly into a biologic molecule synthesizer. The resulting synthesized oligonucleotide sequences can be used in a shuffling reaction, or in a gene synthesizer for parallel gene synthesis. In order to more clearly describe the invention, and to provide a specific description of possibly preferred embodiments, this section discusses example input formats and example results formats according to specific embodiments of the invention. These examples are not intended to limit the invention.

Further Example Input Data File Formats

Gene or Partial Gene Sequence Data

As will be understood from the teachings herein, the most straightforward input data will comprise one or more gene sequences or indications of gene sequences. Such sequences are commonly expressed in digital data as a list of the letters A, C, T, or G, representing the four DNA base pairs. Other letters can be used for encoding RNA and for encoding degenerate locations. As is known in the art and will be understood from the teachings herein, diversity generation operations generally utilize data expressed as nucleotide bases. However, according to specific embodiments of the invention, data can be transmitted by the client as data indicating one or more polypeptide sequences, and a variety of different back translation techniques, such as those discussed in co-assigned patent applications, can be employed as part of diversity generation operations performed at a server according to specific embodiments of the invention.

Polypeptide Sequence Data

According to specific embodiments of the present invention, input may be received from a client in the form of data representing polypeptide sequences. A number of data formats are known for transmitting such data. FIG. 1 illustrates an example of a partial input data file in MSF format that may be used according to specific embodiments of the invention. While this example shows an aligned format of multiple polypeptide sequences (corresponding to SEQ ID NO: 1 and SEQ ID NO: 2), alternatively, an unaligned set of sequences can be provided, with the service provider supplying an alignment during the diversity generation operation. Also, a single sequence can be provided, with a user indicating desired added diversity locations or indicating directions for locating additional sequences from other databases. Thus, the input can include deterministic data (e.g., produced by parallel synthesis) and/or wet lab (e.g., recombination or mutation-derived) data.

Protein Structure Data

FIG. 2 illustrates an example of a partial input data file in PDB format (depicting sequences corresponding to SEQ ID NOS: 3-12) that may be used according to specific embodiments of the invention. As will be understood in the art, such a data representation can provide sequence and structural data regarding one or more polypeptide sequences.

Chemical Structure Data

FIG. 3 illustrates an example of a partial input data in SMILES format (depicting sequences corresponding to SEQ ID NOS: 13-22) that may be used according to specific embodiments of the invention. As will be understood in the art, such a data representation can provide chemical structure data and sequences for any number of organic molecules, including polypeptides and/or oligonucleotides.

Chemical Reaction Data

According to further specific embodiments of the present invention, an input data file can include further data. For example, an input data file might specify a desired chemical reaction, with the reactants and produces specified in a SMILES format, and with further indications requesting an enzyme that will either promote or inhibit the desired reaction. As a different example, input data can include a PDB data file, with a request that the sequence be shuffled with other sequences exhibiting a range of thermal properties. Other examples of possible input data formats will be understood to those of skill in the art from the teachings provided herein.

Sequence or Structure Plus Goal

According to further specific embodiments of the present invention, an input data file can indicate a one or more parent sequences, such as by any of the methods discussed above, and can further indicate a desired goal or change to the compound. For example, the input data may indicate a polypeptide or oligonucleotide sequence corresponding to an enzyme of a desired activity optimized in a neutral pH environment with a goal that the activity be maximized in an acid environment. A diversity generation operation could be used to analyze the sequence and using other data either create a systematically varied library of clones that would be predicted likely to exhibit the desired activity or return as a result an identification of positions that are predicted to be likely diversity targets to achieve the desired activity.

Results Data Formats

Oligonucleotides

FIG. 4 illustrates an example of a partial output data file of oligonucleotides that may be provided according to specific embodiments of the invention. As will be understood to those of skill in the art from the teachings provided herein, such a file can be provided to a customer as a results file. Such data can also be directed by a customer to be delivered directly to a synthesis and/or shuffling machine for shuffling of the oligonucleotides. Such a file can also be used by a server system to prepare a set of oligonucleotides for delivery to a client. It will be understood from the teachings provided herein that sequences provided to a client system to facilitate or enable a shuffling reaction may not include all of the sequences needed for the reaction. For example, a set of returned oligonucleotides may include only bridging oligonucleotides that enable a further diversity generation operation at the client site using one or more parent sequences that reside at the client or are obtained by the client other than from the server system.

Shuffling Parameters

FIG. 5 illustrates an example of a partial output data file of shuffling parameters that may be provided according to specific embodiments of the invention. As will be understood to those of skill in the art from the teachings provided herein, such a file can be provided to a customer as a results file. Such data can also be directed by a customer to be delivered directly to a synthesis and/or shuffling machine to enable a diversity generating reaction.

Machine Instructions

FIG. 6 illustrates an example of a partial output data file of machine instructions according to specific embodiments of the invention. Such an output can be used to direct the actions of an automated shuffling and/or synthesis machine, for example as described in coassigned patent applications. For example, the output may be directed to a synthesis machine for parallel gene synthesis using ligation-based or polymerase-based gene assembly methods. See, e.g. WO 90/00626; Sandhu, et al., Biotechniques, 12(1):14-16 (1992); Dillon, et al., Biotechniques, 9(3):298-300 (1990); Chen, et al., J. Am. Chem. Soc. 116:8799-8800 (1994); Prodromou, et al., Protein Engineering, 5(8):827-829 (1992).

Structure Coordinates

FIG. 7 illustrates an example of a partial output data file of structure coordinates that may be provided according to specific embodiments of the invention.

Residues/Positions of Interest

A further example result output according to specific embodiments of the present invention would be indications of the positions of the parent sequences that are of interest to be varied. Such positions could then be used at the client site as an initial point for creating systematically varied libraries of interest.

Results Provided in Physical Form

According to specific embodiments of the present invention, results can also be provided to a customer/client in the form of a physical preparation of a systematically varied library of biologic molecules. These systematically varied libraries may be provided in arrays or cassettes containing separated systematically varied library molecules or mixtures of molecules. Such arrays can contained a few, to dozens, to 1,000 or more wells or locations each containing a different variant or mixture of variants according to specific embodiments of the present invention. For example, a result delivered to a client can comprise a cassette containing arrayed libraries of protein variants. A cassette, according to specific embodiments of the present invention, can also contain fluidic and detection systems, which in combination with an appropriately configured reader (serving as a user interface to fluidics and detection, as well as environmental control system) would allow a user to perform relatively simple assays. For example, according to specific embodiments of the invention, a cassette along with a reader is supplied to allow a customer to perform a first screen for lead candidates. Coordinates of the compound or mixture on such an array can be used to identify a clone or subset of clones in a systematically varied library. Once identified, the particular lead compounds can be further sold or licensed to customers for further testing or further shuffling technology can be used to further tailor identified leads to meet customer desired characteristics.

Thus, according to further embodiments of the present invention, a variety of physical products can be provided to customers using the teachings provided herein, including such things as biological molecules, arrays or cassettes containing multiple molecules or groups of libraries of molecules, etc. Alternatively, the invention according to specific embodiments can be embodied in immobilized arrays of shuffled polypeptides or oligonucleotides comprising a systematically varied protein library.

Further information regarding diversity generation operations, including structural design and analysis of polypeptides can be found iter alia in published PCT applications WO00/47612 and WO00/23564, U.S. Pat. Nos. 6,188,965 and 6,269,312, and references cited therein.

2. Providing Systematically Varied Libraries Over a Network

Figure 8B:
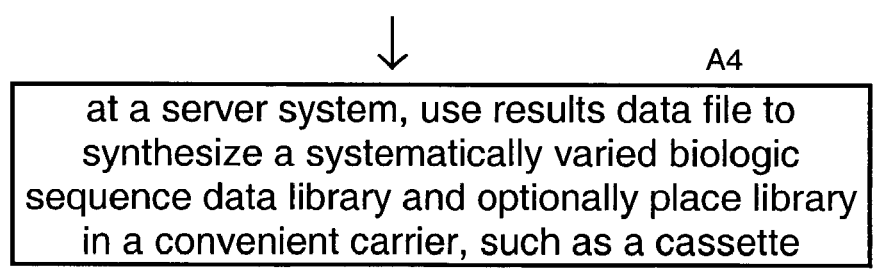

FIG. 8A-B are flow charts illustrating methods of providing systematically varied library results using a network according to specific embodiments of the invention. In one embodiment, a server system receives a request and input data from a client system (Step A1). According to specific embodiments of the present invention, data and/or indications can be transmitted to the server using any method for transmitting digital data, including HTML communications, FTP communications, email communications, etc. In various embodiments, indications of a desired diversity generating analysis or operation can be received from a human user selecting from a graphical interface at a computing device, as described elsewhere herein. The human user can also indicate one or more initial data sets. For example, a user may indicate a data file InputData1.dat, such as the examples illustrated above. In different embodiments, data may be submitted automatically by processing equipment at a client site. For example, a nucleic acid or protein handling synthesis or screening system may be programmed to forward data to a server according to specific embodiments of the present invention to perform specific diversity generation analyses.

Once the request is received at a server system, it is generally analyzed and optionally various messages can be sent back to a client system (Step A2). These messages can comprise either a confirmation stating that the request was received and will be processed or can include a request for further information. For example, for a recombination reaction, generally two different initial data sets are required. According to specific embodiments of the invention, if a client submits just one data set, a server can request additional data sets be submitted. According to further embodiments, a server can indicate available intermediate files that it can use to generate the recombination results and seek confirmation from the client that use other of the present invention or can request. These messages could include confirmation of acceptance of licensing or intellectual property rights before completing the analysis.

Once the server system has sufficient information and/or confirmations from the client system, an analysis or operation component of the server system performs the requested or operation (Step A3).

When the desired analysis or operation is complete, according to specific embodiments of the present invention, the server returns the results. According to specific embodiments of the present invention, these results are returned as electronic data (Step A4). For example, for a recombination analysis, one or more data files representing selected shuffled sequences are returned. Alternatively, a system or method according to specific embodiments of the present invention can use the indicated operation or analysis to prepare physical polypeptides or oligonucleotides in a systematically varied library to deliver to the user (FIG. 8B).

Thus, the present invention enables a method for a client user to receive biologic results, including recombination analysis results, over a communication network from a remote analysis system. These results can also be used to make biological molecules, or libraries of such molecules, which can be ordered by the client and delivered to the client in a physical form, such as one or more synthesized biological molecules.

3. Diversity Generation Operations

A variety of diversity generating techniques that can be used by a server system according to specific embodiments of the invention are available and described in the art. Other techniques are described in coassigned patent applications or may be developed or modified in the future. Thus, the present invention according to specific embodiments can use any known or yet to be developed diversity generation operation. Various diversity generation operation can be used separately and/or in combination to produce one or more variants of a nucleic acid or set of nucleic acids (or oligonucleotides), as well variants of encoded proteins (or polypeptides). Individually and collectively, these procedures provide robust, widely applicable ways of generating diversified sequences (e.g. nucleic acids, sets of nucleic acids (including, e.g., nucleic acid libraries), polypeptides, or sets of polypeptides) useful, e.g., for the engineering or rapid evolution of nucleic acids, proteins, pathways, cells and/or organisms with new and/or improved characteristics. While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties, or that encode proteins with or which confer desirable properties. Following diversification by one or more of the methods herein, or otherwise available to one of skill, any nucleic acids that are produced can be selected for encoding and distribution according to specific embodiments of the present invention. This can include identifying any activity that can be detected, for example, in an automated or automatable format, by any of the assays in the art prior to encoding and distribution as described herein.

Descriptions of a variety of diversity generating procedures for generating modified nucleic acid sequences are found in the following publications and the references cited therein: Soong, N. et al. (2000) "Molecular breeding of viruses" *Nat Genet* 25(4):436-439; Stemmer, et al. (1999) "Molecular breeding of viruses for targeting and other clinical properties" *Tumor Targeting* 4:1-4; Ness et al. (1999) "DNA Shuffling of subgenomic sequences of subtilisin" *Nature Biotechnology* 17:893-896; Chang et al. (1999) "Evolution of a cytokine using DNA family shuffling" *Nature Biotechnology* 17:793-797; Minshull and Stemmer (1999) "Protein evolution by molecular breeding" *Current Opinion in Chemical Biology* 3:284-290; Christians et al. (1999) "Directed evolution of thymidine kinase for AZT phosphorylation using DNA family shuffling" *Nature Biotechnology* 17:259-264; Crameri et al. (1998) "DNA shuffling of a family of genes from diverse species accelerates directed evolution" *Nature* 391:288-291; Crameri et al. (1997) "Molecular evolution of an arsenate detoxification pathway by DNA shuffling," *Nature Biotechnology* 15:436-438; Zhang et al. (1997) "Directed evolution of an effective fucosidase from a galactosidase by DNA shuffling and screening" *Proc. Natl. Acad. Sci. USA* 94:4504-4509; Patten et al. (1997) "Applications of DNA Shuffling to Pharmaceuticals and Vaccines" *Current Opinion in Biotechnology* 8:724-733; Crameri et al. (1996) "Construction and evolution of antibody-phage libraries by DNA shuffling" *Nature Medicine* 2:100-103; Crameri et al. (1996) "Improved green fluorescent protein by molecular evolution using DNA shuffling" *Nature Biotechnology* 14:315-319; Gates et al. (1996) "Affinity selective isolation of ligands from peptide libraries through display on a lac repressor 'headpiece dimer'" *Journal of Molecular Biology* 255: 373-386; Stemmer (1996) "Sexual PCR and Assembly PCR" In: *The Encyclopedia of Molecular Biology*. VCH Publishers, New York. pp. 447-457; Crameri and Stemmer (1995) "Combinatorial multiple cassette mutagenesis creates all the permutations of mutant and wildtype cassettes" *BioTechniques* 18:194-195; Stemmer et al., (1995) "Single-step assembly of a gene and entire plasmid form large numbers of oligodeoxyribonucleotides" *Gene*, 164:49-53; Stemmer (1995) "The Evolution of Molecular Computation" *Science* 270: 1510; Stemmer (1995) "Searching Sequence Space" *Bio/Technology* 13:549-553; Stemmer (1994) "Rapid evolution of a protein in vitro by DNA shuffling" *Nature* 370:389-391; and Stemmer (1994) "DNA shuffling by random fragmentation and reassembly: In vitro recombination for molecular evolution." *Proc. Natl. Acad. Sci. USA* 91:10747-10751.

Mutational methods of generating diversity include, for example, site-directed mutagenesis (Ling et al. (1997) "Approaches to DNA mutagenesis: an overview" *Anal Biochem.* 254(2): 157-178; Dale et al. (1996) "Oligonucleotide-directed random mutagenesis using the phosphorothioate method" *Methods Mol. Biol.* 57:369-374; Smith (1985) "In vitro mutagenesis" *Ann. Rev. Genet.* 19:423-462; Botstein & Shortle (1985) "Strategies and applications of in vitro mutagenesis" *Science* 229:1193-1201; Carter (1986) "Site-directed mutagenesis" *Biochem. J.* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" *Proc. Natl. Acad. Sci. USA* 82:488-492; Kunkel et al. (1987) "Rapid and efficient site-specific mutagenesis without phenotypic selection" *Methods in Enzymol.* 154, 367-382; and Bass et al. (1988) "Mutant Trp repressors with new DNA-binding specificities" *Science* 242:240-245); oligonucleotide-directed mutagenesis (*Methods in Enzymol.* 100:468-500 (1983); *Methods in Enzymol.* 154: 329-350 (1987); Zoller & Smith (1982) "Oligonucleotide-directed mutagenesis using M13-derived vectors: an efficient and general procedure for the production of point mutations in any DNA fragment" *Nucleic Acids Res.* 10:6487-6500; Zoller & Smith (1983) "Oligonucleotide-directed mutagenesis of DNA fragments cloned into M13 vectors" *Methods in Enzymol.* 100: 468-500; and Zoller & Smith (1987) "Oligonucleotide-directed mutagenesis: a simple method using two oligonucleotide primers and a single-stranded DNA template" *Methods in Enzymol.* 154:329-350); phosphorothioate-modified DNA mutagenesis (Taylor et al. (1985) "The use of phosphorothioate-modified DNA in restriction enzyme reactions to prepare nicked DNA" *Nucl. Acids Res.* 13: 8749-8764; Taylor et al. (1985) "The rapid generation of oligonucleotide-directed mutations at high frequency using phosphorothioate-modified DNA" *Nucl. Acids Res.* 13: 8765-8787 (1985); Nakamaye & Eckstein (1986) "Inhibition of restriction endonuclease Nci I cleavage by phosphorothioate groups and its application to oligonucleotide-directed mutagenesis" *Nucl. Acids Res.* 14: 9679-9698; Sayers et al. (1988) "Y-T Exonucleases in phosphorothioate-based oligonucleotide-directed mutagenesis" *Nucl. Acids Res.* 16:791-802; and Sayers et al. (1988) "Strand specific cleavage of phosphorothioate-containing DNA by reaction with restriction endonucleases in the presence of ethidium bromide" *Nucl. Acids Res.* 16: 803-814); mutagenesis using gapped duplex DNA (Kramer et al. (1984) "The gapped duplex DNA approach to oligonucleotide-directed mutation construction"

Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16:6987-6999).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundström et al. (1985) "Oligonucleotide-directed mutagenesis by microscale 'shotgun' gene synthesis" Nucl. Acids Res. 13: 3305-3316), double-strand break repair (Mandecki (1986) "Oligonucleotide-directed double-strand break repair in plasmids of Escherichia coli: a method for site-specific mutagenesis" Proc. Natl. Acad. Sci. USA, 83:7177-7181; and Arnold (1993) "Protein engineering for unusual environments" Current Opinion in Biotechnology 4:450-455). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications and applications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" PCT/US00/26708 by Welch et al., "Use of Codon-Varied Oligonucleotide Synthesis for Synthetic Shuffling;" and PCT/US01/06775 "Single-Stranded Nucleic Acid Template-Mediated Recombination and Nucleic Acid Fragment Isolation" by Affholter.

In brief, several different general classes of sequence modification methods, such as mutation, recombination, etc. can be used at a server system as described herein according to specific embodiments of the present invention. The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants is described in several of the references above, e.g., in Stemmer (1994) Proc. Natl. Acad. Sci. USA 91:10747-10751.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above.

Whole genome recombination methods can also be used in which whole genomes of cells or other organisms are recombined, optionally including spiking of the genomic recombination mixtures with desired library components (e.g., genes corresponding to the pathways of the present invention). These methods have many applications, including those in which the identity of a target gene is not known. Details on such methods are found, e.g., in WO 98/31837 by del Cardayre et al. "Evolution of Whole Cells and Organisms by Recursive Sequence Recombination;" and in, e.g., PCT/US99/15972 by del Cardayre et al., also entitled "Evolution of Whole Cells and Organisms by Recursive Sequence Recombination."

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Olgonucleotide Mediated Nucleic Acid Recombination;" PCT/US00/26708 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

According to specific embodiments of the invention, methods of recombination can be performed digitally on an information processing system. For example, algorithms can be used in a computer to recombine sequence strings that correspond to homologous (or even non-homologous) biologic molecules. According to specific embodiments of the invention, after processing in a computer system, the resulting sequence strings can be converted into nucleic acids by synthesis of nucleic acids which correspond to the recombined sequences, e.g., in concert with oligonucleotide synthesis/gene reassembly techniques. This approach can generate random, partially random or designed variants. Many details regarding various embodiments of computer enabled recombination, including the use of various algorithms, operators and the like in computer systems, as well as combinations of designed nucleic acids and/or proteins (e.g., based on crossover site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding computer (e.g., in silico) recombination methods are found in these applications.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. These methods can be used in physical systems or can be performed in computer systems according to specific embodiments of the invention. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. Additional details regarding this approach are found, e.g., in "Single-Stranded Nucleic Acid Template-Mediated Recombination and Nucleic Acid Fragment Isolation" by Affholter, PCT/US01/06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

Mutagenesis employing polynucleotide chain termination methods have also been proposed (see e.g., U.S. Pat. No. 5,965,408, "Method of DNA reassembly by interrupting synthesis" to Short, and the references above), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and reannealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) "A combinatorial approach to hybrid enzymes independent of DNA homology" *Nature Biotech* 17:1205. This approach can be used to generate an initial a library of variants which can optionally serve as a substrate for one or more in vitro or in vivo recombination methods. See, also, Ostermeier et al. (1999) "Combinatorial Protein Engineering by Incremental Truncation," *Proc. Natl. Acad. Sci. USA,* 96: 3562-67; Ostermeier et al. (1999), "Incremental Truncation as a Strategy in the Engineering of Novel Biocatalysts," *Biological and Medicinal Chemistry,* 7: 2139-44.

Mutational methods which result in the alteration of individual nucleotides or groups of contiguous or non-contiguous nucleotides can be favorably employed to introduce nucleotide diversity, prior to preparing a sequence for encoding. Many mutagenesis methods are found in the above-cited references; additional details regarding mutagenesis methods can be found in following, which can also be applied to the present invention. For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11-15 and Caldwell et al. (1992) *PCR Methods Applic.* 2:28-33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Oligonucleotide directed mutagenesis can be used to introduce site-specific mutations in a nucleic acid sequence of interest. Examples of such techniques are found in the references above and, e.g., in Reidhaar-Olson et al. (1988) *Science,* 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Recursive ensemble mutagenesis is a process in which an algorithm for protein mutagenesis is used to produce diverse populations of phenotypically related mutants, members of which differ in amino acid sequence. This method uses a feedback mechanism to monitor successive rounds of combinatorial cassette mutagenesis. Examples of this approach are found in Arkin & Youvan (1992) *Proc. Natl. Acad. Sci. USA* 89:7811-7815.

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548-1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g., Schellenberger U.S. Pat. No. 5,756,316 and the references above). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which, include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., Peterson et al. (1998) U.S. Pat. No. 5,783,431 "METHODS FOR GENERATING AND SCREENING NOVEL METABOLIC PATHWAYS," and Thompson, et al. (1998) U.S. Pat. No. 5,824,485 METHODS FOR GENERATING AND SCREENING NOVEL METABOLIC PATHWAYS) and their use to identify protein activities of interest has been proposed (In addition to the references noted above, see, Short (1999) U.S. Pat. No. 5,958,672 "PROTEIN ACTIVITY SCREENING OF CLONES HAVING DNA FROM UNCULTIVATED MICROORGANISMS"). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful (e.g., functional) and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombined CDRs derived from B cell cDNA libraries can be amplified and assembled into framework regions (e.g., Jirholt et al. (1998) "Exploiting sequence space: shuffling in vivo formed complementarity determining regions into a master framework" *Gene* 215: 471) prior to diversifying according to any of the methods described herein.

Libraries can be biased towards nucleic acids which encode proteins with desirable enzyme activities. For example, after identifying a clone from a library which exhibits a specified activity, the clone can be mutagenized using any known method for introducing DNA alterations. A library comprising the mutagenized homologues is then screened for a desired activity, which can be the same as or different from the initially specified activity. An example of such a procedure is proposed in Short (1999) U.S. Pat. No. 5,939,250 for "PRODUCTION OF ENZYMES HAVING DESIRED ACTIVITIES BY MUTAGENESIS." Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods be applied to the present invention as well. Random or semi-random mutagenesis using doped or degenerate oligonucleotides is also described in, e.g., Arkin and Youvan (1992) "Optimizing nucleotide mixtures to encode specific subsets of amino acids for semi-random mutagenesis" *Biotechnology* 10:297-300; Reidhaar-Olson et al. (1991) "Random mutagenesis of protein sequences using oligonucleotide cassettes" *Methods Enzymol.* 208:564-86; Lim and Sauer (1991) "The role of internal packing interactions in determining the structure and stability of a protein" *J. Mol. Biol.* 219:359-76; Breyer and Sauer (1989) "Mutational analysis of the fine specificity of binding of monoclonal antibody 51F to lambda repressor" *J. Biol. Chem.* 264:13355-60); and "Walk-Through Mutagenesis" (Crea, R; U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., Quick-Change™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation operations used, a result according to specific embodiments of the invention can be recombined (with each other, or with related (or even unrelated) sequences) to produce a diverse set of recombinant nucleic acids, including, e.g., sets of homologous nucleic acids, as well as corresponding polypeptides.

4. Other Example Operations According to Specific Embodiments

As further examples and elaboration on the above, according to specific embodiments of the invention, a server system is able to perform one or more diversity generation operations using an information processing system. As discussed above, these operations can include operations that add diversity to or shuffle sequences to produce one or more new sequences. These operations can also include operations that analyze input data to determine parameters related to or facilitating shuffling. A variety of discreet operations may be used in some instances to prepare results to deliver as directed by the client. Various aspects of these other operations are described in detail in co-assigned U.S. patent applications. Examples of these other operations include (1) Shufflability Calculation (2) Degenerate Oligonucleotide Design, (3) Recombination Identifying Crossover Points, and/or (4) Identification of Relevant Diversity. See also, U.S. Ser. Nos. 60/339,886, filed Nov. 1, 2001; 60/316,812, filed Aug. 31, 2001 and 60/392, 511, filed Jun. 27, 2002.

5. Using Intermediate and/or Proprietary Data and/or Routines

According to further specific embodiments of the invention, an operation according to the invention can utilize intermediate and/or proprietary data and/or proprietary routines or subroutines. For example a particular operation request can involve recombination of non-homologous parents. In order to perform such a recombination, according to specific embodiments of the present invention, a server system may use one or more synthetic intermediate homologues. These intermediate homologues may be compounds that are held proprietary by the server system or another party. According to specific embodiments of the present invention, these proprietary homologues can be kept confidential at the server system, with only the results provided to the end-user. Similarly, a recombination of non-homologous parents according to further embodiments of the present invention, can use intermediate homologues from nature, and in some embodiments, the specific identity of these homologues may not be made known to an end user.

Figure 9:
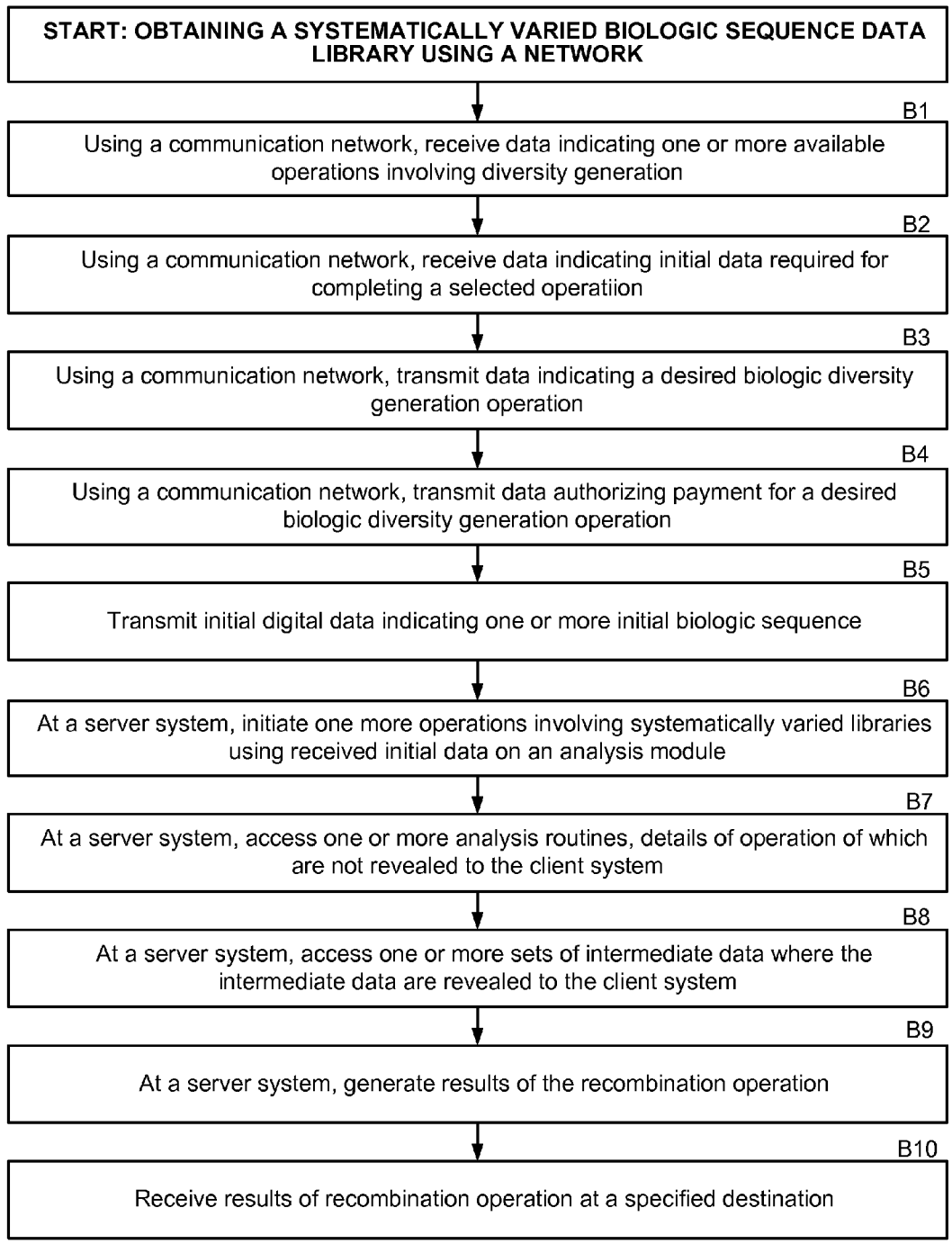
FIG. 9 is a flow chart illustrating a method of obtaining a systematically varied library according to specific embodiments of the present invention.
Figure 9:
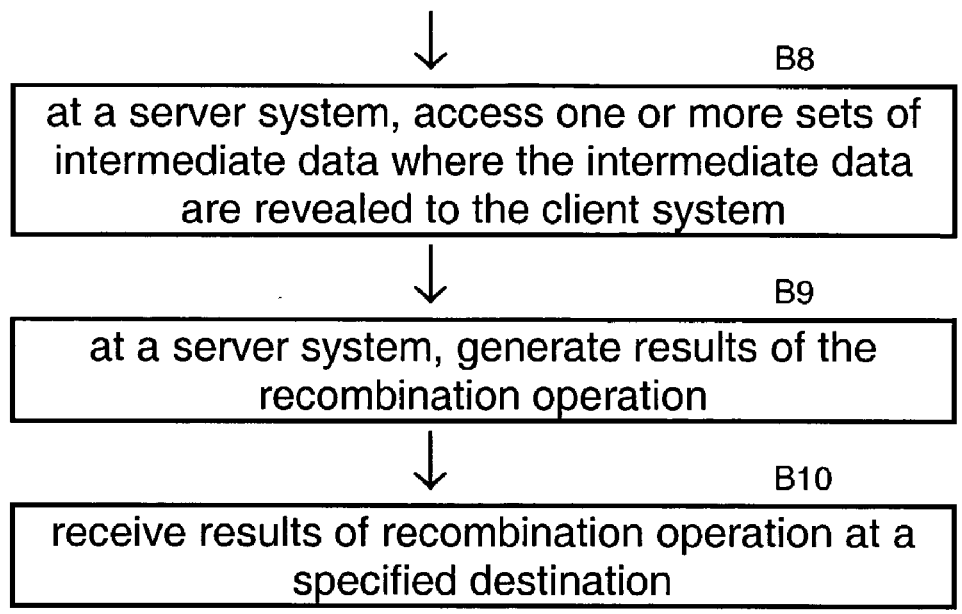

6. Further Detailed Example Method According to Specific Embodiments of the Invention FIG. 9 is a flow chart illustrating a method of obtaining a systematically varied library according to specific embodiments of the present invention. As will be understood from the teachings provided herein, this method contains a number of optional steps that are not necessarily present in all embodiments.

7. Example Interface for Accessing Analysis Over a Network

Figures 10D, 11:
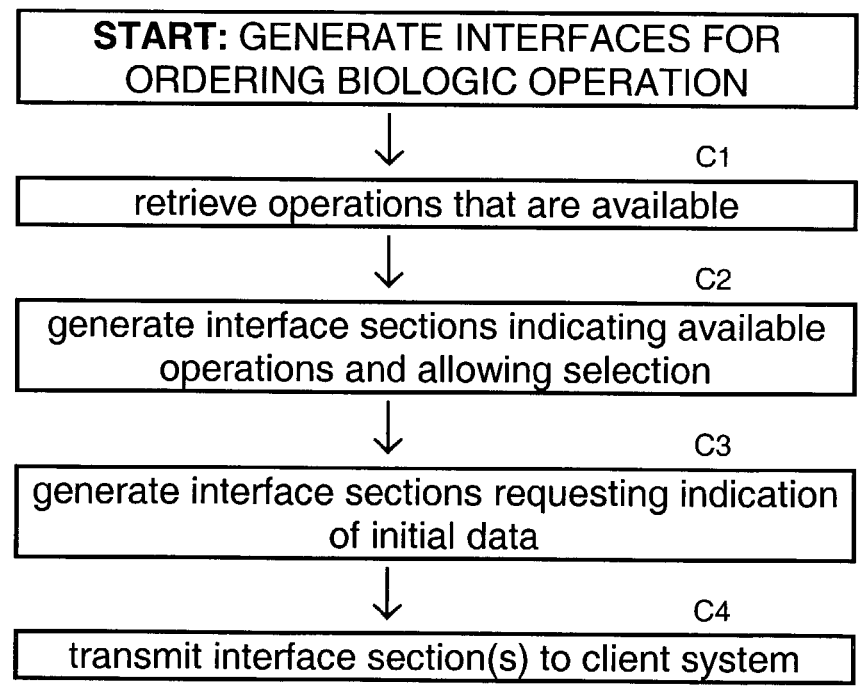

FIG. 10A-D are block diagrams illustrating example graphical interfaces according to specific embodiments of the present invention FIG. 10A illustrates the display of a Web page for one or more operations. According to specific implementations and/or embodiments of the present invention, this example Web page is sent from the server system to the client system when a user accessed the server system. This example Web page contains an operation selection section 101*a-d*, allowing a user to select one or more analyses, a License and Intellectual Property Rights Statement section 102, and a user identification section 103. One skilled in the art would appreciate that these various sections can be omitted or rearranged or adapted in various ways. The 101 section(s) provide information that identifies and describes the biologic operations that may be requested. The 103 section provides a conventional capability to enter account information or payment information or login information. The server system adds the 101 sections to Web pages for each biologic operation that is provided. (One skilled in the art would appreciate that a single Web page on the server system may contain all these sections but that various sections can be selectively included or excluded before sending the Web page to the client system.)

In FIG. 10B optional section 105 allows the user to specify one or more initial sequence data sets on which the desired recombination action will be performed. Such a data input section contains a attachment/upload button 105 or alternatively a sequence input field allowing a user to attach an initial sequence data file.

FIG. 10C illustrates the display of a Web page providing additional information about an analysis request according to specific embodiments of the present invention. As indicated, in this Web page, a user can be informed that certain intermediate data may be used to perform an analysis. This data may be used according to a variety of licensing provisions, discussed further herein.

When client inputs have been specified, the client system sends the data to the server system requesting that the operation be performed. After the server system processes the analysis request, the server system can provide to the client system a new Web page that confirms receipt of the analysis request and can provide additional information such as the time it will take to process the request or the cost for processing the request.

FIG. 10D illustrates the display of a Web page confirming an analysis request. The confirming Web page can contain various information pertaining to the order and can optionally include a confirmation indication allowing a user to make a final confirmation to proceed with the analysis. For particular systems or analysis, this page may also include warnings regarding use of proprietary data or methods and can include additional license terms, such as any rights retained by the owner of the server system in either the submitted initial data, and/or the results data, and/or any intermediate data.

8. Example Interface Method for Accessing Analysis Over a Network

FIG. 11 is a flow diagram of a routine performed at a server system to generate interfaces that allow a customer to access recombination or analysis operations according to specific embodiments of the present invention. According to this example method, a server system retrieves operations that are available (Step B1) and generates interface sections indicating available operations and allowing selection (Step B2). The server also generates interface sections requesting indication of initial data when required (Step B3) and, as needed transmits interface section(s) to a client system (Step B4). As will be understood to those of skill in the art from the teachings provided herein, these interfaces can comprise web pages for display on a browser to a human operator at a client side, for example as shown in FIG. 10 or other interfaces such as audio menus that can be operated over a telephone. Alternatively can comprise interfaces in any suitable computer language or format that can communicate with a programmed client side information handling system.

Figure 12:
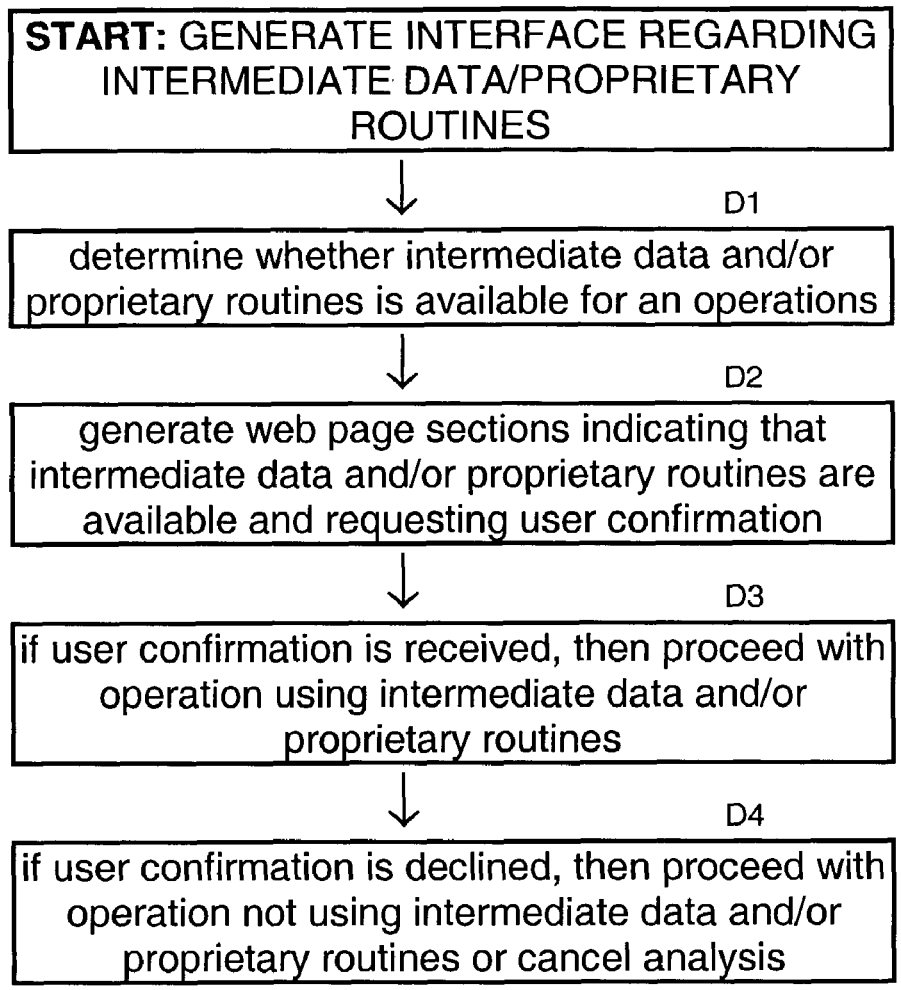
FIG. 12 is a flow diagram of a routine that enables a customer to accept or decline licensing associated with intermediate data according to specific embodiments of the present invention.

Similarly, FIG. 12 is a flow diagram of a routine that enables a customer to accept or decline licensing associated with intermediate data according to specific embodiments of the present invention. Typically, the interfaces generated according to the method illustrated in FIG. 12 will be web pages or similar interfaces, such as an audio menu that can be accessed over a telephone, that allows a human operator at the client side the opportunity to view and modify operation options related to intermediate data and/or routines. Alternatively, these interfaces can be constructed in any suitable computer language or format that allows response from a programmed client side information handling system.

9. Libraries of New Varied Molecules Derived from Existing Sequences

Figure 13:
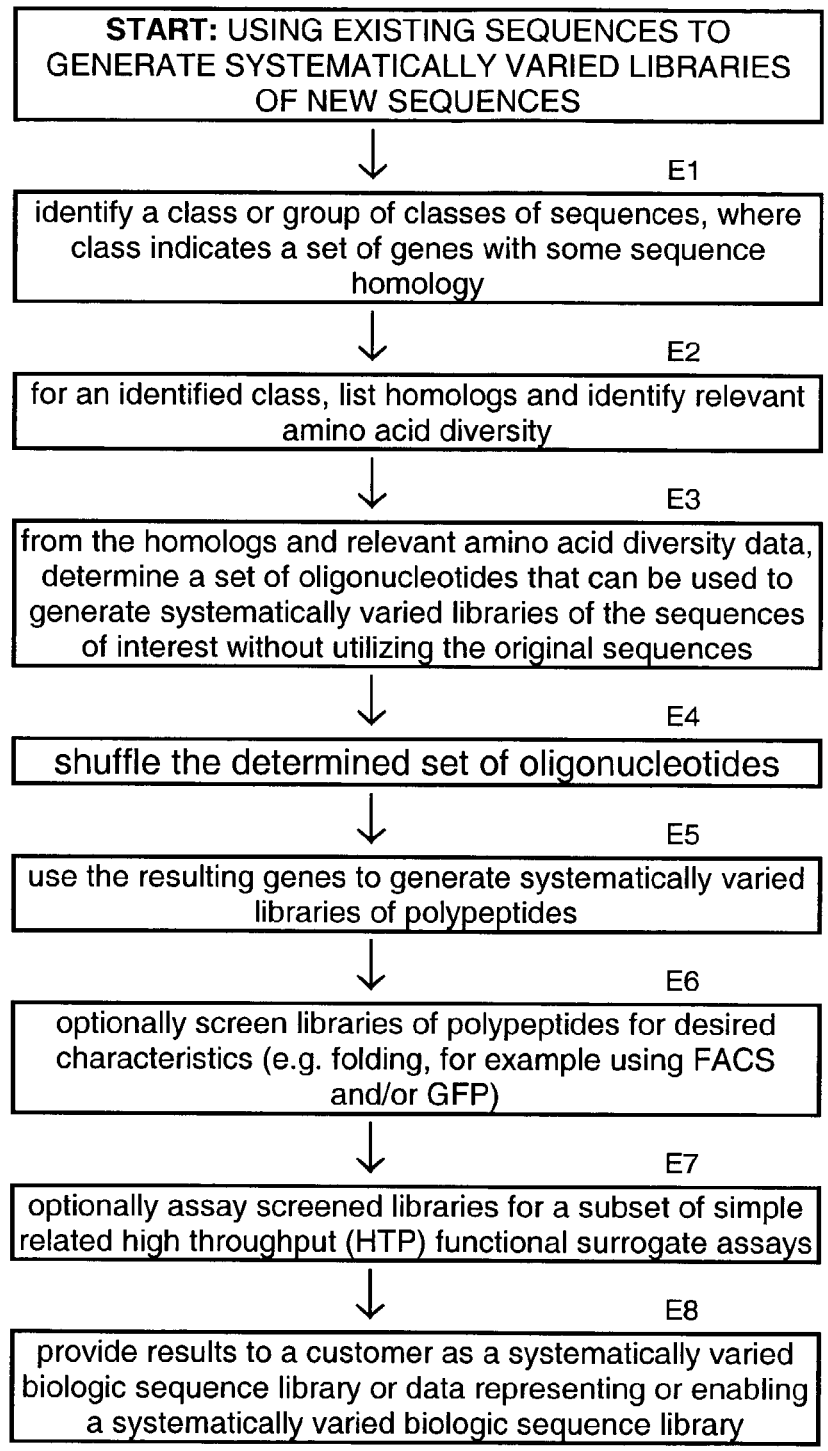
FIG. 13 is a flow diagram of a routine for deriving systematically varied libraries using preexisting sequence data.
Figure 14:
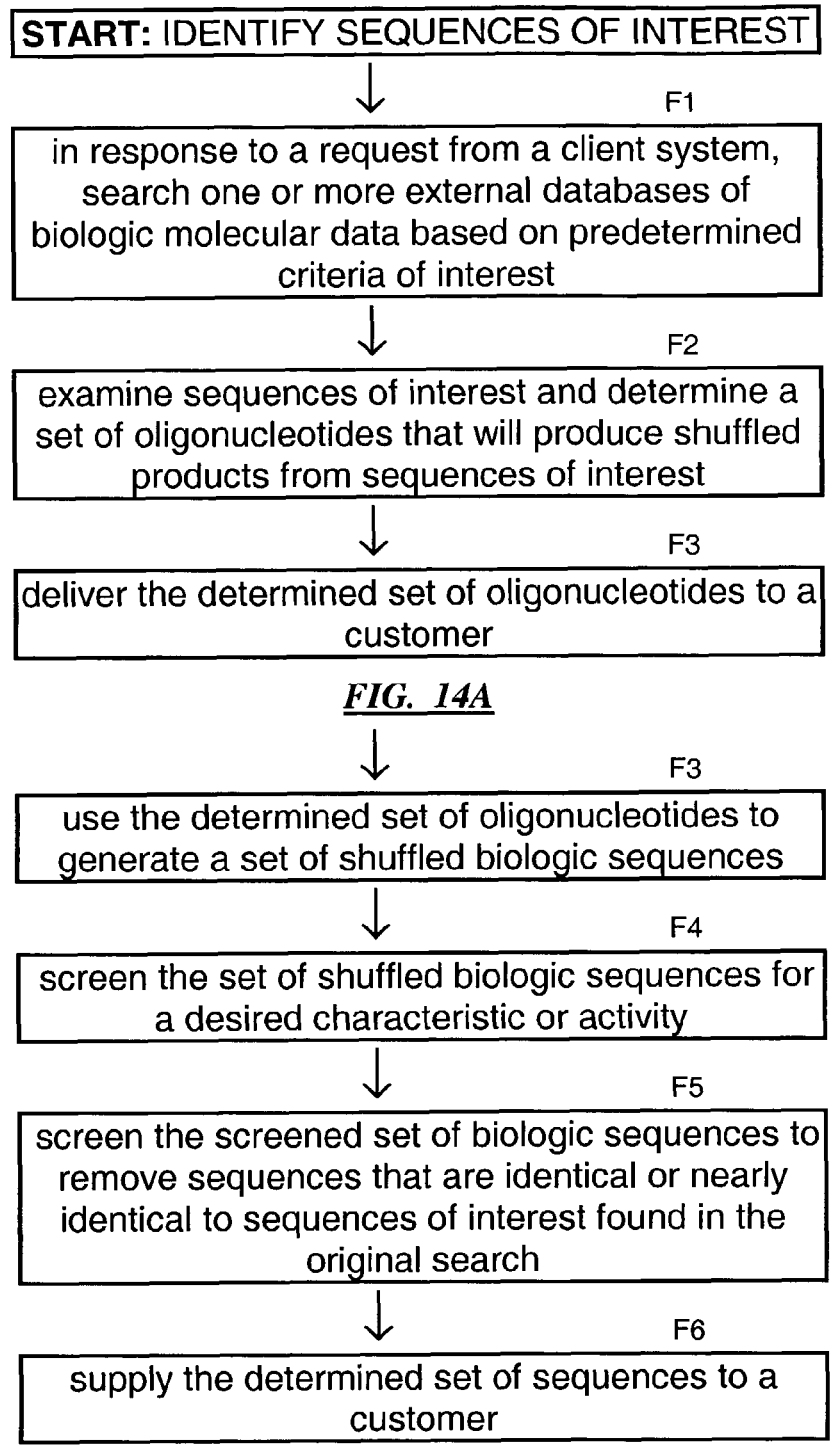
FIG. 14A-B are flow diagrams of optional routines for using preexisting sequence data classes of interest to prepare libraries of new biologic sequences.

An example method related to specific embodiments of the present invention is illustrated in FIG. 13. This method can use the operations and methods described herein to generate a result comprising a systematically varied library of biologic sequences or molecules according to specific embodiments of the invention.

10. Example System Embodiment

Figure 15:
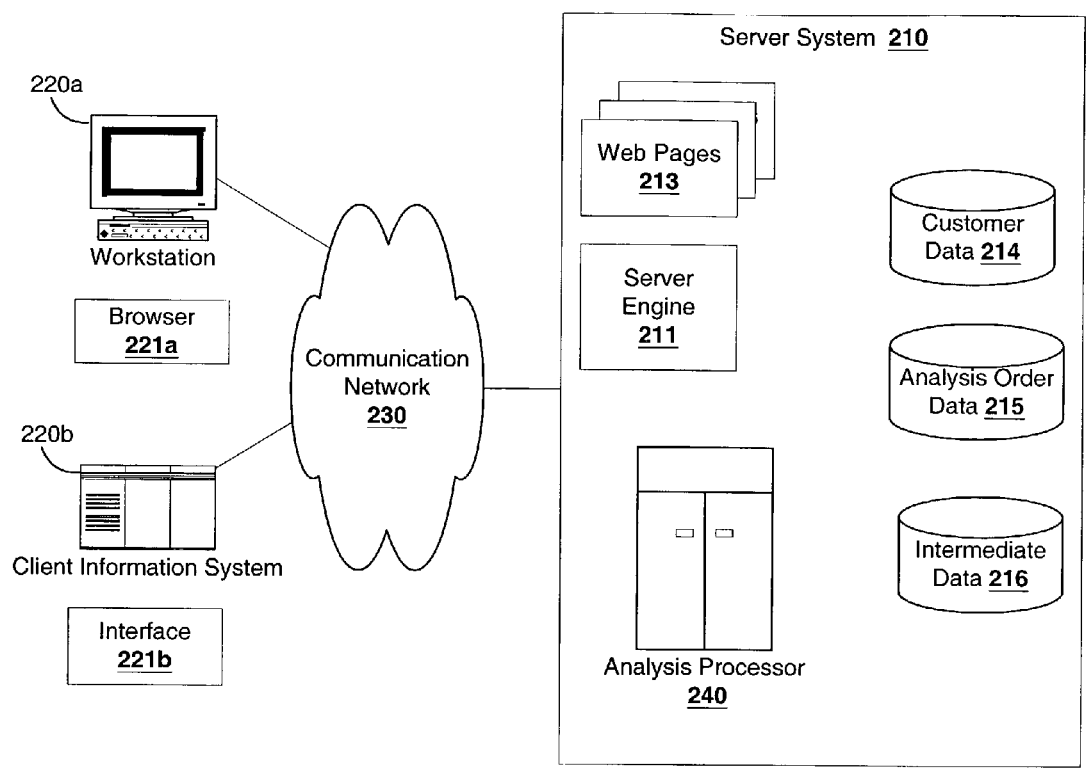
FIG. 15 is a block diagram illustrating various embodiments of the present invention as a system for ordering and delivering biologic operation results.

FIG. 15 is a block diagram illustrating various embodiments of the present invention as a system for ordering and delivering biologic operation results. This particular example embodiment supports providing biologic operations over the Internet. The server system 210 includes a server engine 211, various Web pages 213, an optional customer database 214, and an order tracking database 215. According to specific embodiments of the invention, the server system further includes or is in communication with a processor 240 that further comprises one or more biologic operation module and can optionally access one or more sets of intermediate data 216.

One skilled in the art would appreciate that the technique for providing biologic operations and data results can be used in various environments other than the Internet. For example, providing biologic operations can also be provided in an electronic mail environment in which initial data is submitted in an electronic mail message along with an indication of the desired analysis that is to be performed. Also, various communication channels may be used such as local area network, wide area network, or point-to-point dial up connection. Also, a server system may comprise any combination of hardware and/or software that can process requests for biologic operation in response to client requests. A client system may also comprise any combination of hardware and/or software that can interact with the server system. These systems may include digital workstation or computer systems (an example of which is shown as 220a) including a logic interface module (such as 221a) and/or various other systems or products through which data and requests can be communicated to a server system. These systems may also include laboratory-workstation-based systems (an example of which is shown as 220b) including a logic interface module (such as 221b) or various other systems or products through which data and requests can be communicated to a server system.

11. Further Example System Embodiments

Figure 16:
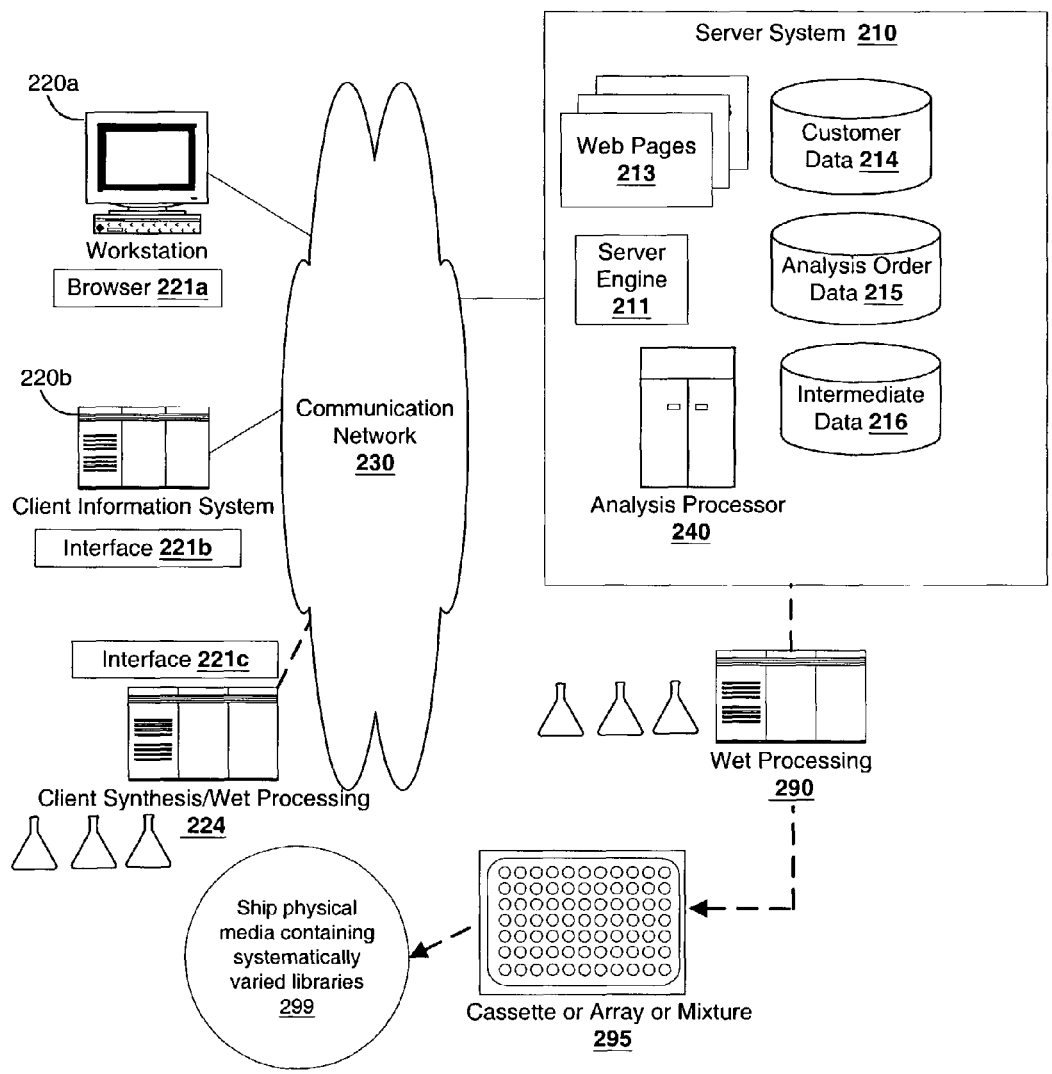
FIG. 16 is a block diagram illustrating an alternative embodiment of the present invention further including wet or physical processing and/or delivery of a physical result.

According to further embodiments of the present invention, the invention can enable more efficient delivery of directed evolution results using in part a communications interface. FIG. 16 is a block diagram illustrating an alternative embodiment of the present invention further including wet or physical processing and/or delivery of a physical result. According to these specific embodiments, the invention may include operation steps that may involve sequence synthesis and/or selection using a "wet" or physical processes at a server side, such as illustrated by synthesis module 290. The results of operations done on a system such as 290 can be used by server system 210 in further processing to produce a digital data result that is transmit back to client system such as 220. Alternatively, a result of a physical processing a system such as 290 can comprise an physical output, such as cassette or array or mixture 295 that can be delivered to a client as a result of an order placed using a communication network.

In a further example embodiment, a server system 210 can transmit digital results to a client physical processing system, such as 224, for some type of physical processing by such a systems. Such digital data can be provided whether or not any physical processing is done at the server side.

While some related services may have previously been provided by, for example, scientific consulting institutions, typically these services have involved considerable expense and have been arranged and engaged on a specific and individual basis. Using the teachings provided herein, the present invention, according to specific embodiments, provides a method allowing customers to more easily order a directed evolution service or directed evolution product and can allow a service provider to provide such services at substantially reduced costs.

12. Embodiment in a Programmed Information Appliance

Figure 17:
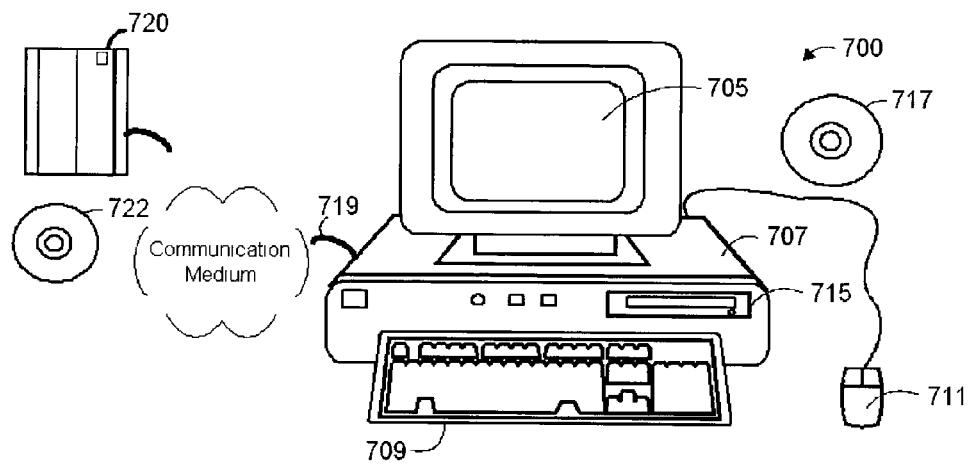
FIG. 17 is a block diagram showing components of a representative example logic device in which various aspects of various specific embodiments of the present invention may be embodied.

FIG. 17 is a block diagram showing components of a representative example logic device in which various aspects of various specific embodiments of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 17 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc.. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

13. Other Embodiments

Although the present invention has been described in terms of various specific embodiments, it is not intended that the invention be limited to the specific example embodiments described herein. Modification within the spirit of the invention will be apparent to those skilled in the art. For example, the server system can be understood as any type of information handling system able to respond to data carried over a communication medium. Such data can be simple digital data, voice commands, telephone key depression data, etc. Likewise, a client system can be understood as any type of information handling system able to send a request over a communication medium to a server system, including such things as a computer, a telephone, or information enabled laboratory or synthesis equipment. Both the client system and/or the server system can include a mixture or combination of cooperating components to effect methods according to specific embodiments of the invention. Likewise, communication channels described herein can include any channels capable of carrying data, including wireless channels, optical channels, and electrical channels.

Thus, it is understood that the examples and embodiments described herein are for illustrative purposes and that various modifications or changes in light thereof will be suggested by the teachings herein to persons skilled in the art and are to be included within the spirit and purview of this application and scope of the claims. All publications, patents, patent applications or other documents cited herein or filed with this application, including any references filed as part of an Information Disclosure Statement included herewith, are incorporated by reference in their entirety.

What is claimed:

1. A method of providing biological data using a communication network comprising:

sending from a server system to a client system over said communication network a set of instructions for displaying, on a user interface of the client system, one or more diversity generation operations available for execution at the server system;

receiving initial data from the client system over said communication network at a server system, said initial data indicating initial biologic sequence characteristics of one or more initial biologic molecules and a request for performing at least one of the one or more diversity generation operations;

sending a confirmation to the client system that the request is complete, said confirmation comprising a warning about proprietary information to be used in analyzing said initial data, said proprietary information is not accessible by the client system;

at said server system, analyzing said initial data and identifying a set of oligonucleotides corresponding to the initial biologic sequence characteristics that can be reassembled into new recombinant nucleic acids, wherein the proprietary information comprises the identified set of oligonucleotides;

at a destination associated with said server system, generating a physical preparation of a systematically varied library by recombining the identified set of oligonucleotides to generate new recombinant nucleic acids; and delivering said physical preparation or sequence data corresponding to sequences in the systematically varied library to a destination associated with said client system.

2. The method of claim 1, wherein said initial data comprises oligonucleotide sequence data of one or more initial oligonucleotides.

3. The method of claim 1, wherein said initial data comprises polypeptide sequence data of one or more initial polypeptides.

4. The method of claim 1, wherein said initial data comprises molecular functional data indicating a desired function of a systematically varied library result.

5. The method of claim 1, wherein said initial data comprises structural data of one or more initial biologic molecules.

6. The method of claim 1, wherein said sequence data corresponding to sequences in the systematically varied library comprises digital data indicating positions or residues of an initial sequence that are good candidates for variation.

7. The method of claim 1, further comprising placing said physical preparation into a carrier for shipment to said destination associated with said client system.

8. The method of claim 7, wherein said carrier comprises a multiwell cassette.

9. The method of claim 7, wherein said carrier comprises a multiwell cassette, each well of said multiwall cassette identified by coordinate data, said coordinate data representing subsets of said systematically varied library.

10. The method of claim 1, wherein said identified set of oligonucleotides comprises a set of degenerate oligonucleotides.

11. The method of claim 1, wherein said identified set of oligonucleotides comprises a set of cross-over oligonucleotides.

12. The method of claim 1 further comprising:
at said server system, authenticating the identity of said client system.

13. The method of claim 1, further comprising:
at said server system, determining a fee for performing the at least one of the one or more diversity generation operations included in said initial data; and
at said server system, verifying client agreement to said fee.

14. The method of claim 1, further comprising, at said server system, ensuring that said initial data is kept secret and is not accessible to any operators of said server system.

15. The method of claim 1, wherein the one or more diversity generation operations available at the server system are selected from the group consisting of calculating shufflability of the one or more initial biologic molecules provided in the initial data, identifying the set of oligonucleotides, indentifying cross-over points, and identifying diversity.

16. The method of claim 1, wherein the server system is configured to receive information from one or more publicly available biologic sequence data banks.

17. The method of claim 1, further comprising requesting information from the one or more publicly available biologic sequence data banks and receiving the requested information from the one or more publicly available biologic sequence data banks.

18. The method of claim 17, wherein the information received from the one or more publicly available biologic sequence data banks is combined with the initial data received from the client system.

19. The method of claim 1, wherein the proprietary information comprises routines and/or subroutines corresponding to the one or more diversity generation operations available for execution at the server system.

20. The method of claim 1, wherein information about the systematically varied library is kept confidential at the server system with access limited to the client system.

* * * * *

SEQUENCE LISTING

<160> NUMBER OF SEQ ID NOS: 22

<210> SEQ ID NO 1
<211> LENGTH: 132
<212> TYPE: PRT
<213> ORGANISM: Human

<400> SEQUENCE: 1

Met Lys Ser Ser Gly Leu Phe Pro Phe Leu Val Leu Ala Leu Gly
 1               5                  10                  15

Thr Leu Ala Pro Trp Ala Val Glu Gly Ser Gly Lys Ser Phe Lys Ala
             20                  25                  30

Gly Val Cys Pro Pro Lys Lys Ser Ala Gln Cys Leu Arg Tyr Lys Lys
             35                  40                  45

Pro Glu Cys Gln Ser Asp Trp Gln Cys Pro Gly Lys Lys Arg Cys Cys
     50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys
                 85                  90                  95

Leu Met Leu Asn Pro Pro Asn Phe Cys Glu Met Asp Gly Gln Cys Lys
             100                 105                 110

Arg Asp Leu Lys Cys Cys Met Gly Met Cys Gly Lys Ser Cys Val Ser
         115                 120                 125

Pro Val Lys Ala
    130

<210> SEQ ID NO 2
<211> LENGTH: 132
<212> TYPE: PRT
<213> ORGANISM: Bacillus sp.

<400> SEQUENCE: 2

Met Leu Gln Ser Ile Pro Ala Leu Pro Val Gly Asp Ile Lys Lys Ser
 1               5                  10                  15

Ile Gly Phe Tyr Cys Asp Lys Leu Gly Phe Thr Leu Val His His Glu
             20                  25                  30

Asp Gly Phe Ala Val Leu Met Cys Asn Glu Val Arg Ile His Leu Trp
             35                  40                  45

Glu Ala Ser Asp Glu Gly Trp Arg Ser Arg Ser Asn Asp Ser Pro Val
     50                  55                  60

Cys Thr Gly Ala Glu Ser Phe Ile Ala Gly Thr Ala Ser Cys Arg Ile
65                  70                  75                  80

Glu Val Glu Gly Ile Asp Glu Leu Tyr Gln His Ile Lys Pro Leu Gly
                 85                  90                  95

Ile Leu His Pro Asn Thr Ser Leu Lys Asp Gln Trp Trp Asp Glu Arg
             100                 105                 110

Asp Phe Ala Val Ile Asp Pro Asp Asn Asn Leu Ile Ser Phe Phe Gln
         115                 120                 125

Gln Ile Lys Ser
    130

<210> SEQ ID NO 3
<211> LENGTH: 13
<212> TYPE: PRT
<213> ORGANISM: Human

```
<400> SEQUENCE: 3

Val Leu Ser Pro Ala Asp Lys Thr Asn Val Lys Ala Ala
1               5                   10

<210> SEQ ID NO 4
<211> LENGTH: 13
<212> TYPE: PRT
<213> ORGANISM: Human

<400> SEQUENCE: 4

Trp Gly Lys Val Gly Ala His Ala Gly Glu Tyr Gly Ala
1               5                   10

<210> SEQ ID NO 5
<211> LENGTH: 13
<212> TYPE: PRT
<213> ORGANISM: Human

<400> SEQUENCE: 5

Arg Val Asp Pro Val Asn Phe Lys Leu Leu Ser His Cys
1               5                   10

<210> SEQ ID NO 6
<211> LENGTH: 13
<212> TYPE: PRT
<213> ORGANISM: Human

<400> SEQUENCE: 6

Leu Leu Val Thr Leu Ala Ala His Leu Pro Ala Glu Phe
1               5                   10

<210> SEQ ID NO 7
<211> LENGTH: 13
<212> TYPE: PRT
<213> ORGANISM: Human

<400> SEQUENCE: 7

Thr Pro Ala Val His Ala Ser Leu Asp Lys Phe Leu Ala
1               5                   10

<210> SEQ ID NO 8
<211> LENGTH: 11
<212> TYPE: PRT
<213> ORGANISM: Human

<400> SEQUENCE: 8

Ser Val Ser Thr Val Leu Thr Ser Lys Tyr Arg
1               5                   10

<210> SEQ ID NO 9
<211> LENGTH: 13
<212> TYPE: PRT
<213> ORGANISM: Human

<400> SEQUENCE: 9

Val His Leu Thr Pro Glu Glu Lys Ser Ala Val Thr Ala
1               5                   10

<210> SEQ ID NO 10
<211> LENGTH: 13
<212> TYPE: PRT
<213> ORGANISM: Human

<400> SEQUENCE: 10
```

Leu Trp Gly Lys Val Asn Val Asp Glu Val Gly Gly Glu
1               5                   10

<210> SEQ ID NO 11
<211> LENGTH: 13
<212> TYPE: PRT
<213> ORGANISM: Human

<400> SEQUENCE: 11

Phe Gly Lys Glu Phe Thr Pro Pro Val Gln Ala Ala Tyr
1               5                   10

<210> SEQ ID NO 12
<211> LENGTH: 13
<212> TYPE: PRT
<213> ORGANISM: Human

<400> SEQUENCE: 12

Gln Lys Val Val Ala Gly Val Ala Asn Ala Leu Ala His
1               5                   10

<210> SEQ ID NO 13
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 13
ctgctgtttc tgttcagctc tgcttattcc cgtggt                          36

<210> SEQ ID NO 14
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 14
ctgctgtttc tgttcagctc tgcttattcc cgtggt                          36

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 15
gagtgagaac acacatagtg ctgctttgtg tggtgccctt attcgtctcg acttgtcttt    60

<210> SEQ ID NO 16
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 16
gtgtttcgtc gtgatacaca caagagtgag gttgctcatc gttttaaaga tttgggcgaa    60

<210> SEQ ID NO 17
<211> LENGTH: 60
<212> TYPE: DNA
<213> ORGANISM: Artificial Sequence -continued

```
<220> FEATURE:
<223> OTHER INFORMATION: Synthetic oligonucleotide

<400> SEQUENCE: 17
ccgttggtca tggtccggaa attttacaag aagcgggttt agaaattttg ctactcgttg    60

<210> SEQ ID NO 18
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 18
gaacatttta aaggcctggt actggttgcc ttttctcagt atctgcagca gtgtccattt    60

<210> SEQ ID NO 19
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 19
atgaagcaag tgattaaaat gtacgagaag tttacctgtg acgacgtcta tgactctttt    60

<210> SEQ ID NO 20
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 20
ctgaaccgtt tgtgcgtgct gcatgagaaa acaccggttt cagaaaaagt cacgaaatgc    60

<210> SEQ ID NO 21
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 21
tcctgctgcc aactggtcgc taaggcacgt cgtaaagcac tgaaaaagac tttggccaca    60

<210> SEQ ID NO 22
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 22
tgcacggaat cgctggtcaa ccgtcgtcct tgcttttctg cgttagaact ggatgaagct    60
```